(12) United States Patent
Hong et al.

(10) Patent No.: US 11,279,673 B2
(45) Date of Patent: Mar. 22, 2022

(54) AROMATIC POLYTHIOL COMPOUND FOR OPTICAL MATERIAL

(71) Applicant: SKC CO., LTD., Gyeonggi-do (KR)

(72) Inventors: Seung Mo Hong, Incheon (KR); Hyeon Myeong Seo, Ulsan (KR); Jongmin Shim, Gyeonggi-do (KR); Sang Mook Kim, Ulsan (KR); Jung Hwan Myung, Seoul (KR); Junghwan Shin, Gyeonggi-do (KR)

(73) Assignee: SKC CO., LTD., Gyeonggi-do (KR)

( * ) Notice: Subject to any disclaimer, the term of this patent is extended or adjusted under 35 U.S.C. 154(b) by 0 days.

(21) Appl. No.: 16/317,408

(22) PCT Filed: Jul. 6, 2017

(86) PCT No.: PCT/KR2017/007249
§ 371 (c)(1),
(2) Date: Jan. 11, 2019

(87) PCT Pub. No.: WO2018/012803
PCT Pub. Date: Jan. 18, 2018

(65) Prior Publication Data
US 2019/0292144 A1  Sep. 26, 2019

(30) Foreign Application Priority Data

Jul. 14, 2016 (KR) .......... 10-2016-0089008
Aug. 31, 2016 (KR) .......... 10-2016-0111537
Aug. 31, 2016 (KR) .......... 10-2016-0111578
Aug. 31, 2016 (KR) .......... 10-2016-0111759

(51) Int. Cl.
| | |
|---|---|
| C08G 75/02 | (2016.01) |
| C07C 321/14 | (2006.01) |
| C07C 319/14 | (2006.01) |
| C08G 75/04 | (2016.01) |
| G02B 1/04 | (2006.01) |
| C08L 81/02 | (2006.01) |
| C08L 75/12 | (2006.01) |
| G03B 3/00 | (2021.01) |
| C07C 319/02 | (2006.01) |
| C08G 18/38 | (2006.01) |
| C08G 18/64 | (2006.01) |
| C08G 18/52 | (2006.01) |

(52) U.S. Cl.
CPC .......... *C07C 321/14* (2013.01); *C07C 319/02* (2013.01); *C07C 319/14* (2013.01); *C08G 18/38* (2013.01); *C08G 18/52* (2013.01); *C08G 18/64* (2013.01); *C08G 75/04* (2013.01); *C08L 75/12* (2013.01); *C08L 81/02* (2013.01); *G02B 1/04* (2013.01); *G02B 1/041* (2013.01); *G03B 3/00* (2013.01)

(58) Field of Classification Search
CPC ...... C07C 321/14; C08G 18/52; C08G 75/04; C08G 75/02

USPC ........................................................ 528/77
See application file for complete search history.

(56) References Cited

U.S. PATENT DOCUMENTS

| | | | | |
|---|---|---|---|---|
| 6,225,439 B1 * | 5/2001 | Amagai | ............... | C08G 59/302 |
| | | | | 528/377 |
| 2003/0195270 A1 | 10/2003 | Ishii et al. | | |
| 2007/0249767 A1 * | 10/2007 | Kang | ................. | C08L 2666/04 |
| | | | | 524/115 |
| 2014/0171612 A1 | 6/2014 | Bojkova et al. | | |
| 2014/0205818 A1 * | 7/2014 | Schwartz | ................. | G03F 7/16 |
| | | | | 428/201 |

FOREIGN PATENT DOCUMENTS

| | | |
|---|---|---|
| EP | 2824126 A1 | 1/2015 |
| JP | 9-12663 A | 1/1997 |
| JP | 2981242 | 11/1999 |
| JP | 2001-139687 A | 5/2001 |
| JP | 3444682 | 9/2003 |
| JP | 2004511578 | 4/2004 |
| JP | 2012-242718 A | 12/2012 |
| JP | 2014-531503 A | 11/2014 |
| JP | 5719486 B1 | 5/2015 |
| KR | 100180926 | 5/1999 |
| KR | 1020030075401 | 9/2003 |
| KR | 1020040063136 | 7/2004 |
| KR | 1020060064859 | 6/2006 |
| KR | 1020100077847 | 7/2010 |
| KR | 101074450 | 10/2011 |
| KR | 1020140141723 | 12/2014 |
| KR | 101594407 | 2/2016 |
| KR | 10-1814724 B1 | 1/2018 |
| WO | 2012/112014 A2 | 8/2012 |

OTHER PUBLICATIONS

Office Action issued by the Korean Intellectual Property Office dated Jan. 23, 2018.
Office Action issued by the Korean Intellectual Property Office dated Jan. 31, 2018.
Extended Search Report issued by European Patent Office dated Jan. 3, 2020.
Office Action issued by Japanese Patent Office dated Dec. 1, 2020.

* cited by examiner

*Primary Examiner* — Gregory Listvoyb
(74) *Attorney, Agent, or Firm* — IP & T Group LLP

(57) ABSTRACT

An embodiment relates to an aromatic polythiol compound for optical materials, and the aromatic polythiol compound according to the embodiment contains a phenyl group and a large number of sulfur atoms in its polythiol structure so that a polymerizable composition and an optical material obtained therefrom have excellent optical properties such as high refractive index and low specific gravity, as well as excellent mechanical properties such as low cure shrinkage; thus, they can be advantageously used for producing various plastic optical lenses such as eyeglass lenses and camera lenses.

2 Claims, No Drawings

AROMATIC POLYTHIOL COMPOUND FOR OPTICAL MATERIAL

This application is a national stage application of PCT/KR2017/007249 filed on Jul. 6, 2017, which claims priority of Korean patent application number 10-2016-0089008 filed on Jul. 14, 2016 and Korean patent application numbers 10-2016-0111537, 10-2016-0111578, 10-2016-0111759 filed on Aug. 31, 2016. The disclosure of each of the foregoing applications is incorporated herein by reference in its entirety.

TECHNICAL FIELD

An embodiment relates to an aromatic polythiol compound used as a raw material for polythiourethane-based optical materials. Other embodiments relate to a polymerizable composition comprising the aromatic polythiol compound and to an optical material produced therefrom.

BACKGROUND ART

Optical materials using plastics are lightweight, hardly breakable, and excellent in dyeability as compared with optical materials made of inorganic materials such as glass. Therefore, plastic materials of various resins are widely used as optical materials for eyeglass lenses, camera lenses, and so on. Recently, due to an increased demand for higher performance and convenience, studies have continued on optical materials having such properties as high transparency, high refractive index, low specific gravity, high heat resistance, and high impact resistance.

Polythiourethane-based compounds are widely used as optical materials owing to their excellent optical properties and mechanical properties. A polythiourethane-based compound may be prepared by reacting a polythiol compound and an isocyanate compound. The physical properties of the polythiol compound significantly affect the physical properties of the polythiourethane-based compound to be prepared.

For example, Korean Patent Nos. 1594407 and 180926 disclose polythiol compounds containing a large number of sulfur (S) atoms. Since these polythiol compounds contain no phenyl group, however, they should be inevitably used with an isocyanate containing a phenyl group in order to synthesize a polythiourethane-based optical material that has high refractive index, low specific gravity, and low cure shrinkage. Further, Korean Patent No. 1074450 discloses a polythiol compound containing a phenyl group. But a polythiourethane-based optical material produced from this polythiol compound does not have sufficient refractive index because the content of sulfur in the polythiol compound is small.

Accordingly, the present inventors have conducted studies to solve the above-mentioned problems and synthesized a bi- or higher-functional, or tetrafunctional, aromatic polythiol compound having a high sulfur content, which can produce a polythiourethane-based compound for an optical material that has excellent physical properties such as refractive index, specific gravity, and cure shrinkage.

DISCLOSURE OF INVENTION

Technical Problem

Accordingly, an embodiment is to provide a bi- or higher-functional, or tetrafunctional, aromatic polythiol compound having a high sulfur content, a polymerizable composition containing the aromatic polythiol compound, and an optical material produced from the same.

Solution to Problem

An embodiment provides an aromatic polythiol compound (A) prepared by reacting a divinylbenzene compound represented by Formula 1 below and a bi- or higher-functional aliphatic polythiol:

[Formula 1]

An embodiment provides an aromatic polythiol compound (B) represented by Formula 2 or 3 below:

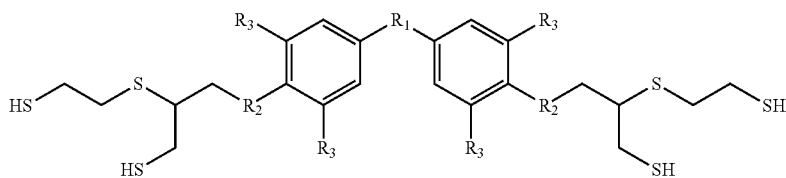

[Formula 2]

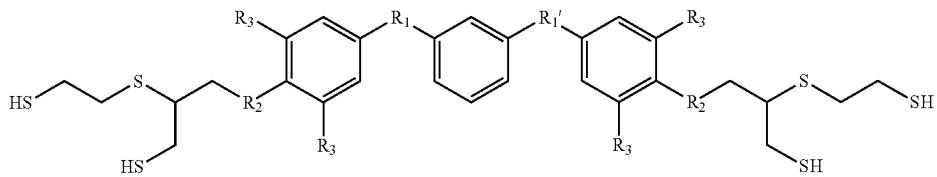

[Formula 3]

In these formulae, $R_1$ and $R_1'$ are each independently a sulfur atom, an oxygen atom, O=S=O, $CX_1Y_1$, or $C=CX_2Y_2$, wherein $X_1$, $Y_1$, $X_2$, and $Y_2$ are each independently a hydrogen atom, a halogen atom, $C_{1-6}$ alkyl, $C_{6-10}$ aryl, $C_{3-6}$ cycloalkyl, or $C_{1-6}$ alkoxy, and wherein $X_1$ and $Y_1$, and $X_2$ and $Y_2$, may combine with each other to form a $C_{3-10}$ ring and may be substituted with at least one selected from the group consisting of a halogen atom, $C_{1-6}$ alkyl, and hydroxy, $R_2$ is each independently an oxygen atom or a sulfur atom, and $R_3$ is each independently a hydrogen atom, a halogen atom, $C_{1-10}$ alkyl, or $C_{6-10}$ aryl.

Further, an embodiment provides a process for preparing a compound represented by Formula 2 below, which comprises (1) reacting a compound represented by Formula 4 below with epichlorohydrin to prepare a compound represented by Formula 5 below; (2) reacting the compound of Formula 5 with 2-mercaptoethanol to prepare a compound represented by Formula 6 below; and (3) reacting the compound of Formula 6 with thiourea and hydrolyzing the reaction product:

[Formula 4]

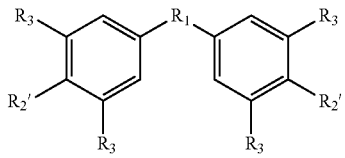

[Formula 5]

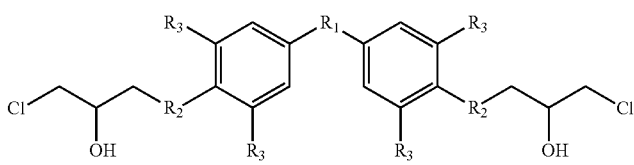

[Formula 6]

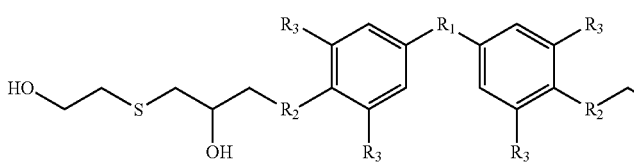

[Formula 2]

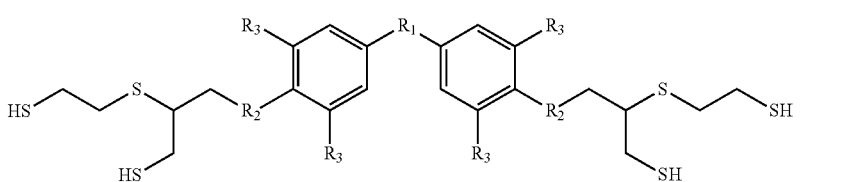

In these formulae, $R_2'$ is each independently hydroxy or thiol, and $R_1$, $X_1$, $Y_1$, $X_2$, $Y_2$, $R_2$, and $R_3$ each are as defined in Formula 2 above.

Further, an embodiment provides a process for preparing a compound represented by Formula 3 below, which comprises (1') reacting a compound represented by Formula 7 below with epichlorohydrin to prepare a compound represented by Formula 8 below; (2') reacting the compound of Formula 8 with 2-mercaptoethanol to prepare a compound represented by Formula 9 below; and (3') reacting the compound of Formula 9 with thiourea and hydrolyzing the reaction product:

[Formula 7]

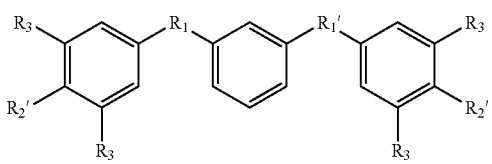

[Formula 8]

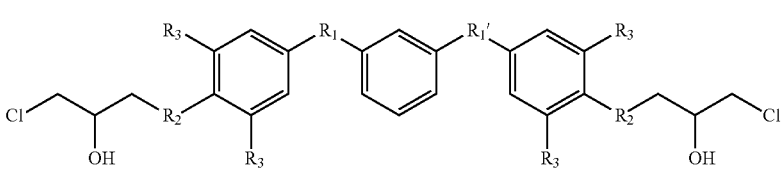

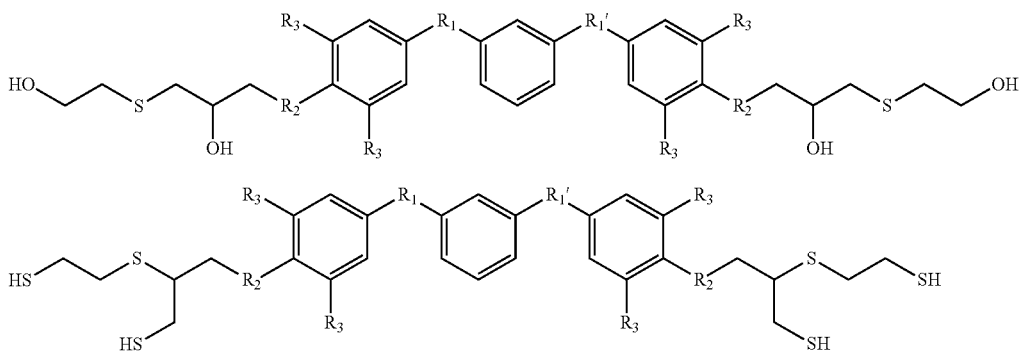

[Formula 9]

[Formula 3]

In these formulae, $R_1$, $R_1'$, $X_1$, $Y_1$, $X_2$, $Y_2$, $R_2$, $R_2'$, and $R_3$ each are as defined in Formulae 3 and 4 above.

An embodiment provides an aromatic polythiol compound (C) represented by Formula 10 below:

[Formula 10]

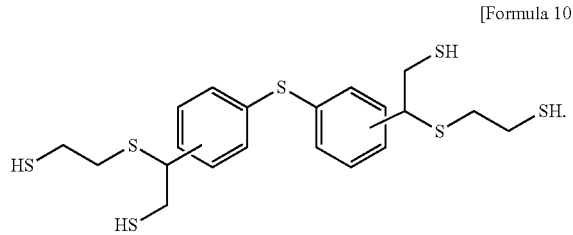

Further, an embodiment provides a process for preparing a compound represented by Formula 10 below, which comprises (1) reacting a compound represented by Formula 11 below with 2-mercaptoethanol to prepare a compound represented by Formula 12 below; (2) reacting the compound of Formula 12 with a metal sulfide to prepared a compound represented by Formula 13 below; and (3) reacting the compound of Formula 13 with thiourea and hydrolyzing the reaction product:

[Formula 10]

[Formula 11]

[Formula 12]

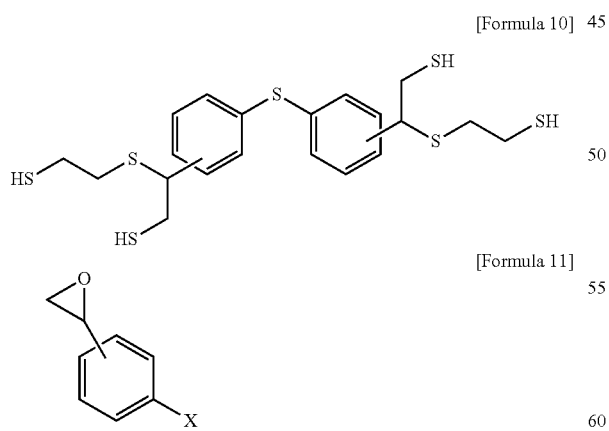

[Formula 13]

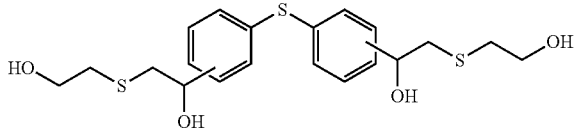

In these formulae, X is a halogen atom.

An embodiment provides an aromatic polythiol compound (D) represented by any one of Formulae 14 to 16 below:

[Formula 14]

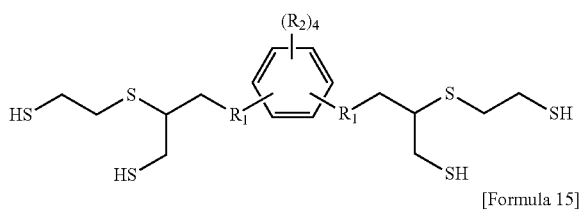

[Formula 15]

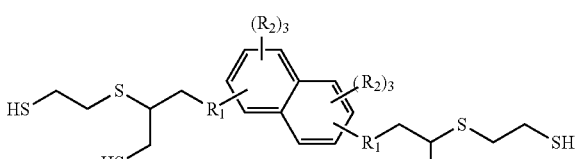

[Formula 16]

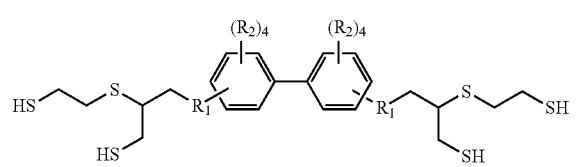

In these formulae, $R_1$ is each independently a sulfur atom or an oxygen atom, and $R_2$ is each independently a hydrogen atom, a halogen atom, $C_{1-10}$ alkyl, or $C_{6-10}$ aryl.

Further, an embodiment provides a process for preparing a compound represented by Formula 14 below, which comprises (1) reacting a compound represented by Formula 17 below with epichlorohydrin to prepare a compound represented by Formula 18 below; (2) reacting the compound of Formula 18 with 2-mercaptoethanol to prepare a compound represented by Formula 19 below; and (3) reacting the compound of Formula 19 with thiourea and hydrolyzing the reaction product:

[Formula 17]

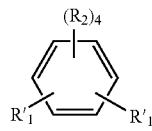

[Formula 18]

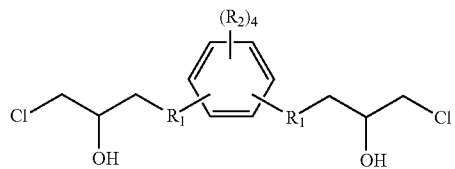

[Formula 19]

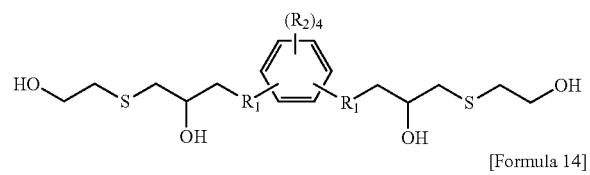

[Formula 14]

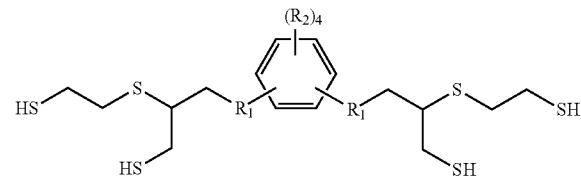

In these formulae, $R_1'$ is each independently hydroxy or thiol, and $R_1$ and $R_2$ each are as defined in Formula 14 above.

Further, an embodiment provides a process for preparing a compound represented by Formula 15 below, which comprises (1') reacting a compound represented by Formula 20 below with epichlorohydrin to prepare a compound represented by Formula 21 below; (2') reacting the compound of Formula 21 with 2-mercaptoethanol to prepare a compound represented by Formula 22 below; and (3') reacting the compound of Formula 22 with thiourea and hydrolyzing the reaction product:

[Formula 20]

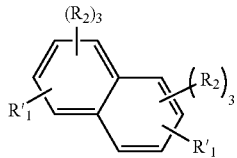

[Formula 21]

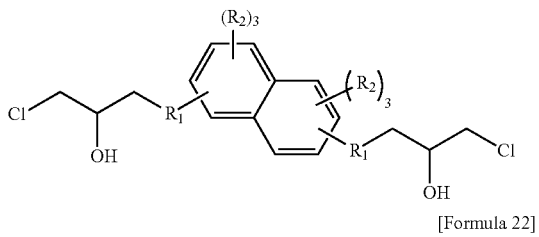

[Formula 22]

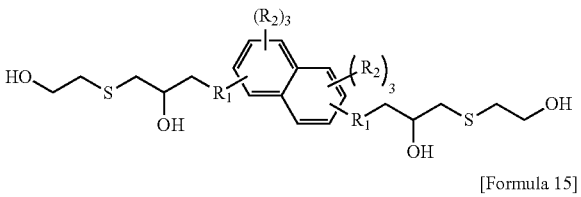

[Formula 15]

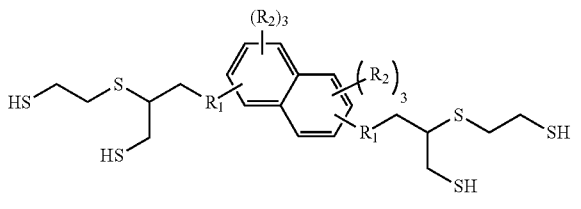

In these formulae, $R_1$, $R_1'$, and $R_2$ each are as defined in Formulae 15 and 17 above.

Further, an embodiment provides a process for preparing a compound represented by Formula 16 below, which comprises (1") reacting a compound represented by Formula 23 below with epichlorohydrin to prepare a compound represented by Formula 24 below; (2") reacting the compound of Formula 24 with 2-mercaptoethanol to prepare a compound represented by Formula 25 below; and (3") reacting the compound of Formula 25 with thiourea and hydrolyzing the reaction product:

[Formula 23]

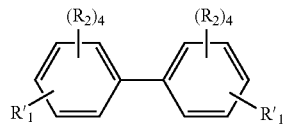

[Formula 24]

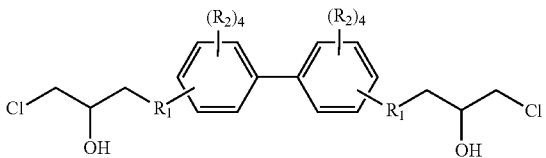

[Formula 25]

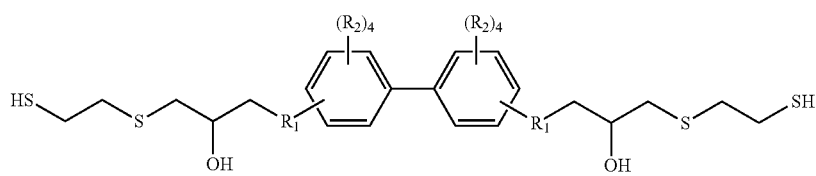

-continued

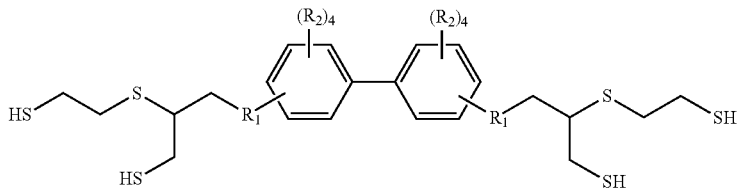
[Formula 16]

In these formulae, $R_1$, $R_1'$ and $R_2$ each are as defined in Formulae 16 and 17 above.

Further, an embodiment provides a polymerizable composition comprising at least one of the aromatic polythiol compounds A to D above and an isocyanate-based compound.

Further, an embodiment provides a process for producing an optical material by polymerizing and molding the polymerizable composition.

Further, an embodiment provides an optical material produced by the above preparation process.

Advantageous Effects of Invention

The aromatic polythiol compounds according to the embodiments contain a phenyl group and a large number of sulfur atoms in their polythiol structures. Therefore, the polymerizable composition and the optical material produced therefrom have excellent optical properties such as high refractive index and low specific gravity, as well as excellent mechanical properties such as low cure shrinkage. They are useful for manufacturing various plastic optical lenses such as eyeglass lenses and camera lenses.

BEST MODE FOR CARRYING OUT THE INVENTION

Hereinafter, the present invention will be described in detail.

The present invention can provide aromatic polythiol compounds having various structures. Here, the aromatic polythiol compounds A, B, C, and D are described according to their structures.

Aromatic Polythiol Compound A

An embodiment provides an aromatic polythiol compound (A) prepared by reacting a divinylbenzene compound represented by Formula 1 below and a bi- or higher-functional aliphatic polythiol:

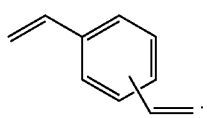
[Formula 1]

The bi- or higher-functional aliphatic polythiol may be prepared by reacting a bi- or higher-functional aliphatic polyol with thiourea and hydrolyzing the reaction product.

First, the bi- or higher-functional aliphatic polyol is reacted with thiourea to prepare an isothiouronium salt, which is hydrolyzed to prepare the bi- or higher-functional aliphatic polythiol. Here, the aliphatic polyol may contain a large number of sulfur atoms or an ester bond in its structure.

Specifically, a bi- or higher-functional aliphatic polyol may be mixed with thiourea with reflux in an acidic condition to prepare an isothiouronium salt. Thiourea may be reacted in 1 to 3 equivalents, particularly 1 to 2 equivalents, per 1 equivalent of hydroxy groups in the polyol. For the acidic condition, an aqueous hydrochloric acid solution, hydrogen chloride gas, or the like may be used. The temperature during the reflux may be 60 to 130° C., particularly 90 to 120° C. The reflux time may be 2 to 24 hours, particularly 2 to 12 hours.

Subsequently, the isothiouronium salt is hydrolyzed in an organic solvent in a basic condition to prepare a bi- or higher-functional aliphatic polythiol. For the basic condition, such basic compounds as sodium hydroxide, potassium hydroxide, sodium carbonate, and ammonia may be used. The basic compound may be reacted in 1.0 to 2.5 equivalents, particularly 1.1 to 2.0 equivalents, per 1 equivalent of the isothiouronium salt. Examples of the organic solvent include toluene, xylene, chlorobenzene, and dichlorobenzene. To suppress formation of by-products, toluene is preferred. The hydrolysis temperature may be 10 to 130° C., particularly 30 to 80° C. The hydrolysis time may be 0.1 to 24 hours, particularly 0.5 to 12 hours.

The bi- or higher-functional aliphatic polythiol thus prepared may be further purified.

For example, it may be subjected to several times of alkali washing and several times of water washing. Impurities or the like remaining in the polythiol can be removed through the washing process, which improves the color of the polythiol and the color of the optical material produced therefrom.

Thereafter, if desired, the bi- or higher-functional aliphatic polythiol may be subjected to drying, filtration, and the like.

Examples of the bi- or higher-functional aliphatic polythiol include methanedithiol, 1,2-ethanedithiol, 1,3-propanedithiol, 1,4-butanedithiol, 1,5-pentanedithiol, 1,6-hexanedithiol, 1,7-heptanedithiol, 1,8-octanedithiol, 1,9-nonanedithiol, 1,10-decanedithiol, 1,1-propanedithiol, 1,2-propanedithiol, 2,2-propanedithiol, 1,6-hexanedithiol, 1,2,3-propanetrithiol, tetrakis(mercaptomethyl)methane, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, bicyclo[2,2,1]pepta-exo-cis-2,3-dithiol, 1,1-bis(mercaptomethyl)cyclohexane, thiomalic acid bis(2-mercaptoethyl ester), 2,3-dimercaptosuccinic acid (2-mercaptoethyl ester), 2,3-dimercapto-1-propanol (2-mercaptoacetate), 2,3-dimercapto-1-propanol (3-mercaptoacetate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl) ether, ethylene glycol bis(2-mercaptoacetate), ethylene glycol bis(3-mercaptopropionate), trimethylolpropane tris(2-mercaptoacetate), pentaerythritol tetrakis(2-mercaptoacetate), pentaerythritol tetrakis(3-mercaptopropionate), 1,2-bis(2-mercaptoethylthio)-3-mercaptopropane, glycol di(mercaptoacetate), glyceryl dithioglycolate, glycol di(3-mercaptopropionate), ethoxylated trimethylol propane tri(3-mercaptopropionate), trimethylolpropane tri(3-mercaptopropionate), tris[2-(3-mercaptopropionyloxy)ethyl] isocyanurate, trimethylolpropane tri(mercaptoacetate), pentaerythritol tetra(3-mercaptopropionate), pentaerythritol tetra(mercaptoacetate), dipentaerythritol hexa(3-mercaptopropionate), 4-mercaptomethyl-1,8-dimercapto-3,6-dithiaoctane, 5,9-dimercaptomethyl-1,13-dimercapto-3,7,11-trithiatridecane; an aliphatic polythiol containing a sulfur atom aside from a mercapto group, which includes hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thioglycolic acid bis(2-mercaptoethyl ester), thiodipropionic acid bis(2-mercaptoethyl ester), 4,4-thiodibutyric acid bis(2-mercaptoethyl ester), dithiodiglycolic acid bis(2-mercaptoethyl ester), dithiodipropionic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercapto propyl ester), dithioglycolic acid bis(2,3-dimercaptopropyl ester), dithiodipropionic acid (2,3-dimercapto propyl ester); a polythiol containing a hydroxyl group aside from a mercapto group, which includes 2-mercaptoethanol, 3-mercapto-1,2-propanediol, glycerin di(mercaptoacetate), 1-hydroxy-4-mercaptocyclohexane, 2-mercapto hydroquinone, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), pentaerythritol pentakis(3-mercaptopropionate), hydroxymethyl-tris(mercaptoethylthiomethyl)methane, 4-hydroxy-4'-mercaptodiphenyl sulfone, 2-(2-mercaptoethylthio)ethanol, dihydroxyethyl sulfide mono(3-mercaptopropionate), dimercaptoethane mono(salicylate), hydroxyethylthiomethyl tris(mercaptoethylthio)methane; bis(mercaptomethyl) sulfide, bis(mercaptoethyl) sulfide, bis(mercaptopropyl) sulfide, bis(mercaptomethylthio)methane, bis(2-mercaptoethylthio)methane, bis(3-mercaptopropyl)methane, 1,2-bis(mercaptomethylthio)ethane, 1,2-(2-mercaptoethylthio)ethane, 1,2-(3-mercaptopropyl)ethane, 1,3-bis(mercaptomethylthio)propane, 1,3-bis(2-mercaptoethylthio)propane, 1,3-bis(3-mercaptopropylthio)propane, 1,2-bis(2-mercaptoethylthio)-3-mercaptopropane, 2-mercaptoethylthio-1,3-propanedithiol, 1,2,3-tris(mercaptomethylthio)propane, 1,2,3-tris(2-mercaptoethylthio)propane, 1,2,3-tris(3-mercaptopropylthio)propane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl) sulfide, 2,5-dimercapto-1,4-dithiane, 2,5-dimercaptomethyl-1,4-dithiane, bis(mercaptomethyl)disulfide, bis(mercaptoethyl)disulfide, bis(mercaptopropyl) disulfide, and their esters of thioglycolic acid and mercaptopropionic acid; and

wherein m is an integer of 2 to 10.

Specifically, the bi- or higher-functional aliphatic polythiol may be glycol di(mercaptoacetate), glyceryl dithioglycolate, glycol di(3-mercaptopropionate), ethoxylated trimethylolpropane tri(3-mercaptopropionate), trimethylolpropane tri(3-mercaptopropionate), tris[2-(3-mercaptopropionyloxy)ethyl]isocyanurate, trimethylolpropane tri(mercaptoacetate), pentaerythritol tetra(3-mercaptopropionate), pentaerythritol tetra(mercaptoacetate), dipentaerythritol hexa(3-mercaptopropionate), 4-mercaptomethyl-1,8-dimercapto-3,6-dithiaoctane, 5,9-dimercaptomethyl-1,13-dimercapto-3,7,11-trithiatridecane, or a mixture thereof.

More specifically, the bi- or higher-functional aliphatic polythiol may be trimethylolpropane tri(3-mercaptopropionate), pentaerythritol tetra(3-mercaptopropionate), 4-mercaptomethyl-1,8-dimercapto-3,6-dithiaoctane, 5,9-dimercaptomethyl-1,13-dimercapto-3,7,11-trithiatridecane, or a mixture thereof.

The bi- or higher-functional aliphatic polythiol as described above may be reacted with the divinylbenzene compound of Formula 1 above to prepare the desired aromatic polythiol compound.

The molar ratio of the divinylbenzene compound to the bi- or higher-functional aliphatic polythiol may be 1:2 to 1:10, 1:2 to 1:6, or 1:2 to 1:3.

The reaction may be carried out in the presence of a radical initiator as a catalyst. Examples of the initiator include an azobisalkylene nitrile-based initiator such as azobisisobutyronitrile (AIBN), 2,2'-azobis(2,4-dimethylvaleronitrile), and 1,1'-azobis(cyclohexanecarbonitrile); and an azo peroxide-based initiator such as benzoyl peroxide, dilauryl peroxide, and cumyl hydroperoxide. The reaction temperature may be, for example, 20 to 110° C., particularly 50 to 100° C. Specific reaction conditions may vary depending on the type of the free radical initiator and may be adjusted in view of the initiation temperature and the half-life of the free radical initiator.

The aromatic polythiol compound prepared from the divinylbenzene compound and the bi- or higher-functional aliphatic polythiol may have a number average molecular weight of 500 to 3,000, 700 to 2,500, or 1,000 to 2,000.

The aromatic polythiol compound contains a phenyl group and a large number of sulfur atoms in its structure. Thus, it may be subsequently reacted with an isocyanate to produce a polythiourethane-based optical material that has excellent optical properties such as high refractive index and low specific gravity, as well as excellent mechanical properties such as low cure shrinkage.

An embodiment provides a polymerizable composition comprising the aromatic polythiol compound (A) and an isocyanate-based compound.

The polymerizable composition may comprise the aromatic polythiol compound in an amount of 100% by weight. If necessary, the polymerizable composition may further comprise a polythiol compound different from the aromatic polythiol compound in addition to the aromatic polythiol compound as described above. When the polymerizable composition further comprises a polythiol compound different from the aromatic polythiol compound, the aromatic polythiol compound may be in an amount of 5 to 70 parts by weight based on 100 parts by weight of the total thiol compounds.

The isocyanate-based compound may be a conventional one commonly used for the synthesis of polythiourethane. Specifically, it may be at least one selected from the group consisting of an aliphatic isocyanate-based compound such as isophorone diisocyanate, dicyclohexylmethane-4,4-diisocyanate, hexamethylene diisocyanate, 2,2-dimethyl pentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecatriisocyanate, 1,3,6-hexamethylene triisocyanate, 1,8-diisocyanate-4-isocyanatomethyloctane, bis(isocyanatoethyl) carbonate, bis(isocyanatoethyl) ether, 1,2-bis(isocyanatomethyl) cyclohexane, 1,3-bis(isocyanatomethyl) cyclohexane, 1,4-bis(isocyanatomethyl) cyclohexane, dicyclohexylmethane diisocyanate, cyclohexane diisocyanate, methylcyclohexane diisocyanate, dicyclohexyldimethylmethane isocyanate, 2,2-dimethyldicyclohexylmethane isocyanate, bis(isocyanatoethyl) sulfide, bis(isocyanatopropyl) sulfide, bis(isocyanatohexyl) sulfide, bis(isocyanatomethyl) sulfone, bis(isocyanatomethyl) disulfide, bis(isocyanatopropyl) disulfide, bis(isocyanatomethylthio)methane, bis(isocyanatoethylthio)methane, bis(isocyanatoethylthio)ethane, bis(isocyanatomethylthio)ethane, 1,5-diisocyanato-2-isocyanatomethyl-3-thiapentane, 2,5-diisocyanatothiophene, 2,5-bis(isocyanatomethyl) thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3-dithiolane, 4,5-bis(isocyanatomethyl)-2-methyl-1,3-dithiolane; and an aromatic isocyanate compound such as bis(isocyanatoethyl)benzene, bis(isocyanatopropyl)benzene, bis(isocyanatobutyl)benzene, bis(isocyanatomethyl)naphthalene, bis(isocyanatomethyl) diphenyl ether, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluene diisocyanate, toluidine diisocyanate, 4,4-diphenylmethane diisocyanate, 3,3-dimethyldiphenylmethane-4,4-diisocyanate, bibenzyl-4,4-diisocyanate, bis(isocyanatophenyl)ethylene, 3,3-dimethoxybiphenyl-4,4-diisocyanate, hexahydrobenzene diisocyanate, hexahydrodiphenylmethane-4,4-diisocyanate, o-xylene diisocyanate, m-xylene diisocyanate, p-xylene diisocyanate, xylene diisocyanate, X-xylene diisocyanate, 1,3-bis(isocyanatomethyl)cyclohexane, diphenyl sulfide-2,4-diisocyanate, diphenyl sulfide-4,4-diisocyanate, 3,3-dimethoxy-4,4-diisocyanatodibenzyl thioether, bis(4-isocyanatomethylbenzene) sulfide, 4,4-methoxybenzenethioethylene glycol-3,3-diisocyanate, diphenyl disulfide-4,4-diisocyanate, 2,2-dimethyl diphenyl disulfide-5,5-diisocyanate, 3,3-dimethyl diphenyl disulfide-5,5-diisocyanate, 3,3-dimethyl diphenyl disulfide-6,6-diisocyanate, 4,4-dimethyldiphenyldisulfide-5,5-diisocyanate, 3,3-dimethoxydiphenyl disulfide-4,4-diisocyanate, 4,4-dimethoxydiphenyl disulfide-3,3-diisocyanate.

Specifically, 1,3-bis(isocyanatomethyl)cyclohexane, hexamethylene diisocyanate, isophorone diisocyanate, xylene diisocyanate, toluene diisocyanate, or the like may be used.

The polymerizable composition may further comprise such additives as an internal mold release agent, a heat stabilizer, a reaction catalyst, an ultraviolet absorber, and a blueing agent, depending on the purpose thereof.

As the ultraviolet absorber, benzophenone, benzotriazole, salicylate, cyanoacrylate, oxanilide, or the like may be used.

The internal release agent may include a fluorine-based nonionic surfactant having a perfluoroalkyl group, a hydroxyalkyl group, or a phosphate ester group; a silicone-based nonionic surfactant having a dimethylpolysiloxane group, a hydroxyalkyl group, or a phosphate ester group; an alkyl quaternary ammonium salt such as trimethylcetylammonium salt, trimethylstearyl salt, dimethylethylcetylammonium salt, triethyldodecylammonium salt, trioctylmethylammonium salt, and diethylcyclohexadodecylammonium salt; and an acidic phosphate ester. It may be used alone or in combination of two or more.

As the reaction catalyst, a known reaction catalyst used in the preparation of a polythiourethane resin may be properly employed. For example, it may be selected from the group consisting of a dialkyltin halide such as dibutyltin dichloride and dimethyltin dichloride; a dialkyltin dicarboxylate such as dimethyltin diacetate, dibutyltin dioctanoate, and dibutyltin dilaurate; a dialkyltin dialkoxide such as dibutyltin dibutoxide and dioctyltin dibutoxide; a dialkyltin dithioalkoxide such as dibutyltin di(thiobutoxide); a dialkyltin oxide such as di(2-ethylhexyl)tin oxide, dioctyltin oxide, and bis(butoxy dibutyltin) oxide; and a dialkyltin sulfide such as dibutyltin sulfide. Specifically, it may be selected from the group consisting of a dialkyltin halide such as dibutyltin dichloride, dimethyltin dichloride, and the like.

As the heat stabilizer, a metal fatty acid salt, a phosphorus compound, a lead compound, or an organotin compound may be used alone or in combination of two or more.

The blueing agent has an absorption band in the wavelength range from orange to yellow in the visible light region and has a function of adjusting the color of an optical material made of a resin. Specifically, the blueing agent may comprise a material that exhibits blue to violet color, but is not particularly limited thereto. Examples of the blueing agent include a dye, a fluorescent whitening agent, a fluorescent pigment, and an inorganic pigment. It may be properly selected in accordance with the properties required for an optical component to be produced and the resin color. The blueing agent may be used alone or in combination of two or more. In view of the solubility in the polymerizable composition and the transparency of the optical material to be produced, a dye is preferably used as the blueing agent. From the viewpoint of the absorption wavelength, the dye may particularly have a maximum absorption wavelength of 520 to 600 nm; and more specifically, a maximum absorption wavelength of 540 to 580 nm. In terms of the structure of the compound, an anthraquinone-based dye is preferable as the dye. The method of adding the blueing agent is not particularly limited, and the blueing agent may be added to the monomers in advance. Specifically, the blueing agent may be dissolved in the monomers or may be contained in a master solution in a high concentration, the master solution being later diluted with the monomers or other additives and then added.

An embodiment provides a process for producing an optical material by polymerizing and molding the polymerizable composition as described above. Further, an optical material produced by the above preparation process is provided.

Specifically, the optical material may be a polythiourethane-based compound. The polythiourethane-based compound is prepared by polymerizing (and curing) the aromatic polythiol compound and the isocyanate compound. The reaction molar ratio of SH groups to NCO groups in the polymerization reaction may be 0.5 to 3.0, particularly 0.5 to 1.5, more particularly 0.8 to 1.5. Further, the above-mentioned reaction catalyst, which is conventionally used in the production of polythiourethane, may be employed in order to control the reaction rate.

More specifically, the optical material may be produced by polymerizing and molding the polymerizable composition.

First, the polymerizable composition is degassed under reduced pressures and then injected into a mold for molding an optical material. Such degassing and mold injection may be carried out in a temperature range of, for example, 20 to 40° C. Once the composition is injected into the mold, polymerization is usually carried out by gradually heating the composition from a low temperature to a high temperature.

The polymerization temperature may be, for example, 20 to 150° C., particularly 25 to 120° C. A reaction catalyst, which is conventionally used in the production of polythiourethane, may be employed in order to control the reaction rate. Specific examples of the reaction catalyst are as exemplified above.

Then, the polythiourethane-based optical material is released from the mold.

The optical material may have various shapes by changing the mold used in the production. Specifically, it may be in the form of an eyeglass lens, a camera lens, a light emitting diode (LED), or the like.

The optical material may have a refractive index of 1.50 to 1.75, 1.55 to 1.70, or 1.60 to 1.70. The optical material may have a specific gravity of 1.15 to 1.25 or 1.20 to 1.25. The optical material may have a heat distortion temperature (Tg) of 100 to 130° C., 105 to 130° C., 105 to 125° C., or 110 to 125° C.

The optical material may preferably be an optical lens, specifically a plastic optical lens.

Aromatic Polythiol Compound B

An embodiment provides an aromatic polythiol compound (B) represented by Formula 2 or 3 below:

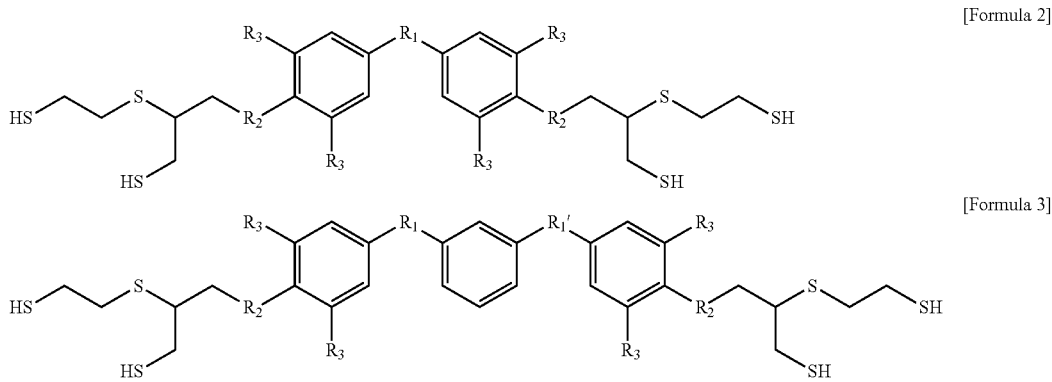

[Formula 2]

[Formula 3]

In these formulae, $R_1$, $R_1'$, $X_1$, $Y_1$, $X_2$, $Y_2$, $R_2$, and $R_3$ each are as defined above.

Specifically, $X_1$ and $Y_1$ are each independently a hydrogen atom, a halogen atom, $C_{1-6}$ alkyl, or $C_{6-10}$ aryl, and $X_2$ and $Y_2$ are each independently a halogen atom. $X_1$ and $Y_1$ may combine with each other to form a $C_{3-10}$ ring. They may be substituted with at least one member selected from the group consisting of a halogen atom and $C_{1-6}$ alkyl.

More specifically, $R_1$ and $R_1'$ are each independently a sulfur atom, an oxygen atom, O=S=O, or $CX_1Y_1$, wherein $X_1$ and $Y_1$ each independently may be a hydrogen atom, a halogen atom, or $C_{1-6}$ alkyl.

The aromatic polythiol compound of Formula 2 or 3 above may be prepared by preparing an aromatic polyol compound from an aromatic compound having two or three phenyl groups and then reacting the aromatic polyol compound with thiourea and hydrolyzing the reaction product.

Specifically, the aromatic polythiol compound of Formula 2 above may be prepared by the steps of (1) reacting a compound represented by Formula 4 with epichlorohydrin to prepare a compound having a structure of chlorohydrin as represented by Formula 5; (2) reacting the compound of Formula 5 with 2-mercaptoethanol to prepare an aromatic polyol compound having a structure of polyhydric alcohol as represented by Formula 6; and (3) reacting the aromatic polyol compound of Formula 6 with thiourea to prepare an isothiouronium salt and hydrolyzing the salt (see Reaction Scheme 1):

[Reaction Scheme 1]

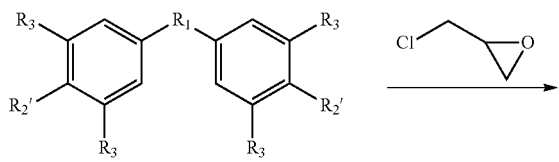

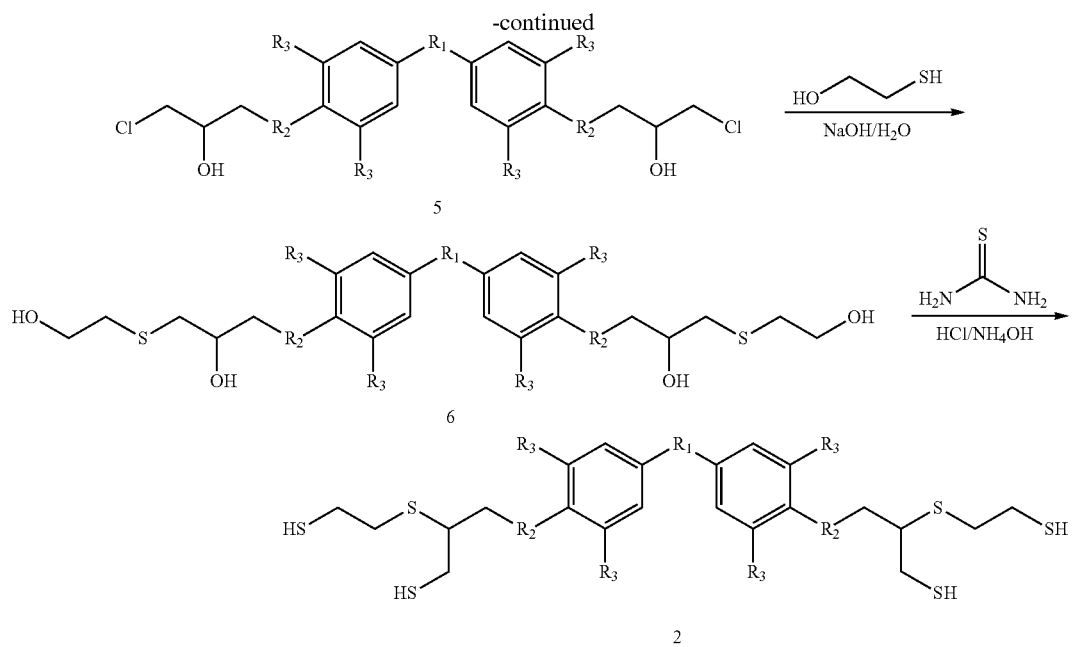

In this scheme, $R_2'$ is each independently hydroxy or thiol, and $R_1$, $X_1$, $Y_1$, $X_2$, $Y_2$, $R_2$, and $R_3$ each are as defined in Formula 2 above.

The aromatic polythiol compound of Formula 3 above may be prepared by the steps of (1') reacting a compound represented by Formula 7 with epichlorohydrin to prepare a compound having a structure of chlorohydrin as represented by Formula 8; (2') reacting the compound of Formula 8 with 2-mercaptoethanol to prepare an aromatic polyol compound having a structure of polyhydric alcohol as represented by Formula 9; and (3') reacting the aromatic polyol compound of Formula 9 with thiourea to prepare an isothiouronium salt and hydrolyzing the salt (see Reaction Scheme 2):

[Reaction Scheme 2]

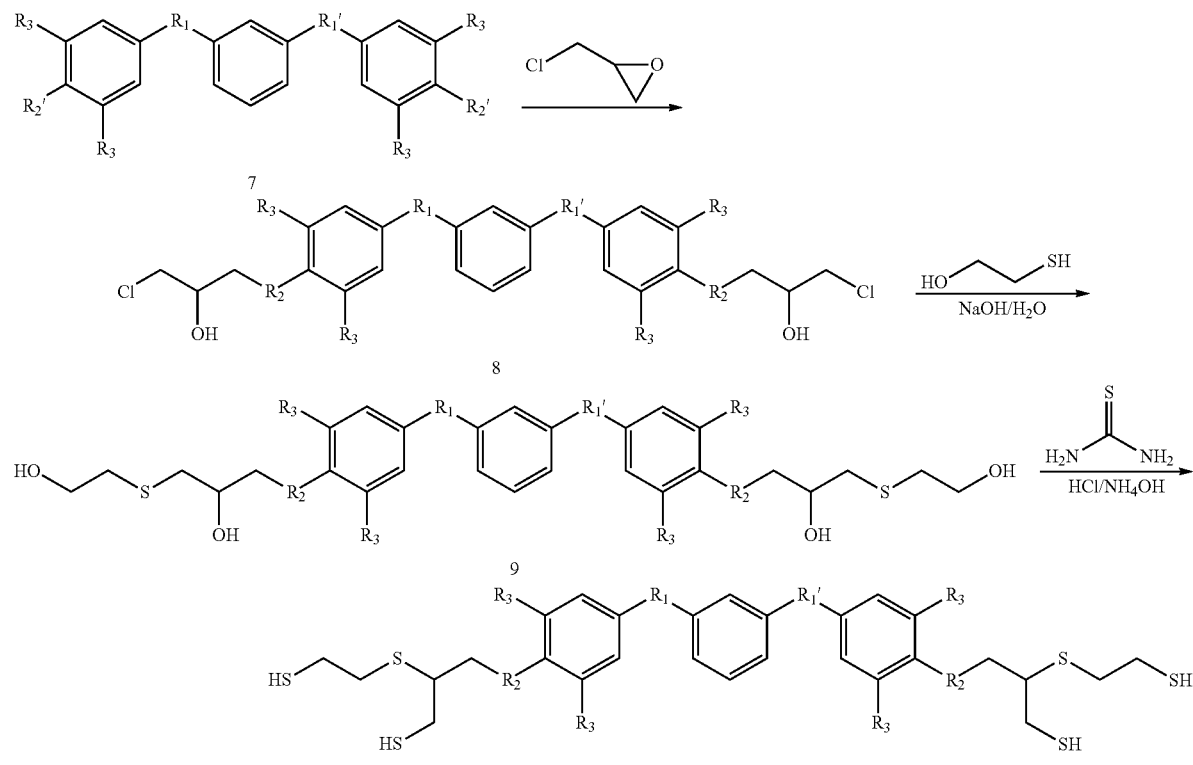

In this scheme, $R_1$, $R_1'$, $X_1$, $Y_1$, $X_2$, $Y_2$, $R_2$, $R_2'$, and $R_3$ each are as defined in Formulae 3 and 4 above.

Steps (1) and (1') above may be carried out in the presence of a catalyst such as triethylamine, sodium hydroxide, potassium hydroxide, chromium octoate, and triphenylphosphine at 40 to 100° C., particularly at 50 to 60° C. Epichlorohydrin may be reacted in an amount of 0.8 to 1.2 equivalents per 1 equivalent of the compound of Formula 4 or 7.

Steps (2) and (2') above may be carried out by reacting the compound of Formula 5 or 8 with 2-mercaptoethanol in water in the presence of a base to obtain the aromatic polyol compound of Formula 6 or 9. As the base, sodium hydroxide; potassium hydroxide; a tertiary amine such as trimethylamine and triethylamine; a secondary amine such as dimethylamine and diethylamine; a primary amine such as methylamine and ethylamine; ammonia; or the like may be used. The reaction may be carried out at 40 to 100° C., particularly at 50 to 60° C. 2-Mercaptoethanol may be reacted in an amount of 0.8 to 1.2 equivalents per 1 equivalent of the compound of Formula 5 or 8.

In steps (3) and (3') above, the aromatic polyol compound of Formula 6 or 9 is mixed with thiourea with reflux in an acidic condition to obtain an isothiouronium salt. Thiourea may be reacted in an amount of 1 to 3 equivalents, particularly 1 to 2 equivalents, per 1 equivalent of hydroxyl group in the aromatic polyol compound. For the acidic condition, an aqueous hydrochloric acid solution, hydrogen chloride gas, or the like may be used. The temperature during the reflux may be 60 to 130° C., particularly 90 to 120° C. The reflux time may be 2 to 24 hours, particularly 2 to 12 hours.

Subsequently, the isothiouronium salt is hydrolyzed in an organic solvent to obtain the aromatic polythiol compound of Formula 2 or 3. Examples of the organic solvent include toluene, xylene, chlorobenzene, and dichlorobenzene. To suppress formation of by-products, toluene is preferred. The hydrolysis temperature may be 10 to 130° C., particularly 30 to 80° C. The hydrolysis time may be 0.1 to 24 hours, particularly 0.5 to 12 hours.

The aromatic polythiol compound thus prepared may be further purified.

For example, it may be subjected to several times of acid washing and several times of water washing. Impurities or the like remaining in the polythiol can be removed through the washing process, which improves the color of the polythiol and the color of the optical material prepared therefrom.

Thereafter, if desired, the aromatic polythiol compound may be subjected to drying, filtration, and the like.

The aromatic polythiol compound prepared above may have a thiol value (SHV or SH value) of 100 to 400 g/eq. Further, the aromatic polythiol compound contains a phenyl group and a large number of sulfur atoms in its structure. Thus, it may be subsequently reacted with an isocyanate to produce a polythiourethane-based optical material that has excellent optical properties such as high refractive index and low specific gravity, as well as excellent mechanical properties such as low cure shrinkage.

An embodiment provides a polymerizable composition comprising the aromatic polythiol compound (B) and an isocyanate-based compound. Here, the polymerizable composition may further comprise a polythiol compound different from the aromatic polythiol compound in addition to the aromatic polythiol compound (B) as described above.

The isocyanate-based compound may be a conventional one commonly used for the synthesis of polythiourethane. Specific examples of the isocyanate-based compound are as exemplified above.

Furthermore, the polymerizable composition may further comprise such additives as an internal mold release agent, a heat stabilizer, a reaction catalyst, an ultraviolet absorber, and a blueing agent, as described above, depending on the purpose thereof.

An embodiment provides a process for producing an optical material by polymerizing and molding the polymerizable composition as described above. Further, an optical material produced by the above preparation process is provided. The optical material may be produced by polymerizing and molding the polymerizable composition in accordance with the process as described above.

Specifically, the optical material is produced by polymerizing (and curing) the aromatic polythiol compound and the isocyanate compound. The reaction molar ratio of SH groups to NCO groups in the polymerization reaction may be 0.5 to 3.0, specifically 0.5 to 1.5, more specifically 0.8 to 1.5. Further, the above-mentioned reaction catalyst, which is conventionally used in the production of polythiourethane, may be employed in order to control the reaction rate.

The optical material may have a refractive index of 1.55 to 1.75, 1.55 to 1.70, 1.59 to 1.75, or 1.59 to 1.70. The optical material may have a specific gravity of 1.10 to 1.30, 1.10 to 1.25, 1.15 to 1.30, 1.15 to 1.25, 1.20 to 1.25, or 1.20 to 1.22. The optical material may have a heat distortion temperature (Tg) of 105 to 130° C., 105 to 120° C., 108 to 130° C., or 108 to 120° C.

The optical material may preferably be an optical lens, specifically a plastic optical lens.

Aromatic Polythiol Compound C

An embodiment provides an aromatic polythiol compound (C) represented by Formula 10 below:

[Formula 10]

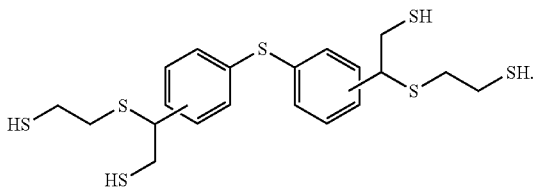

The aromatic polythiol compound of Formula 10 above may be prepared by preparing an aromatic polyol compound from an aromatic compound having a phenyl group and then reacting the aromatic polyol compound with thiourea and hydrolyzing the reaction product.

The aromatic polythiol compound of Formula 10 above may be prepared by the steps of (1) reacting a compound represented by Formula 11 below with 2-mercaptoethanol to prepare a compound represented by Formula 12 below; (2) reacting the compound of Formula 12 with a metal sulfide to prepared a compound represented by Formula 13 below; and (3) reacting the compound of Formula 13 with thiourea and hydrolyzing the reaction product (see Reaction Scheme 3):

[Reaction Scheme 3]

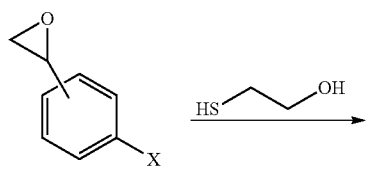

11

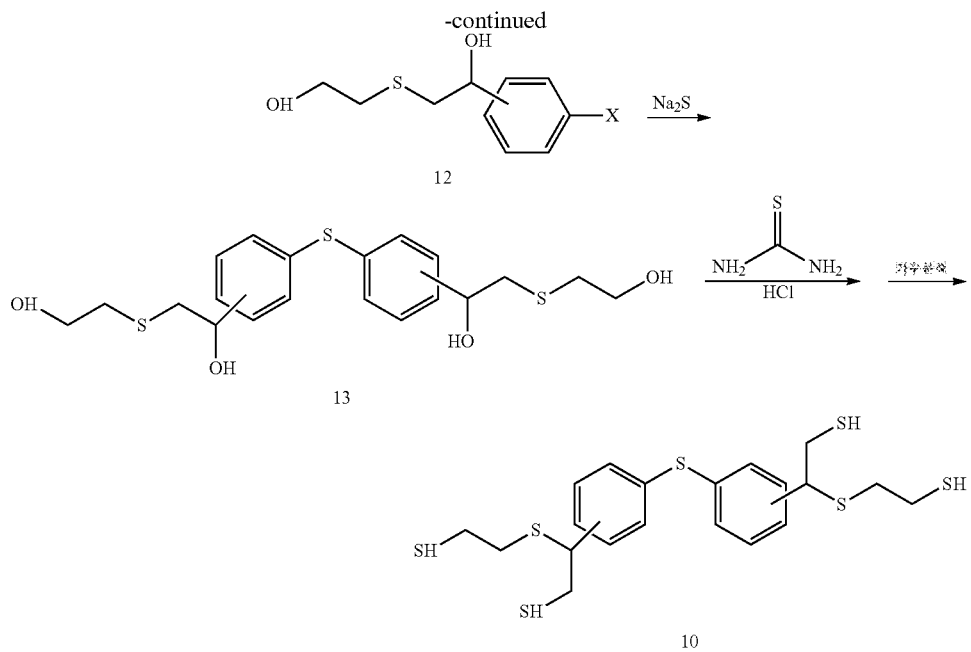

In this scheme, X is a halogen atom, for example, Cl, Br, I, or the like.

Specifically, in step (1) above, the halogenated styrene oxide of Formula 11 is reacted with 2-mercaptoethanol in the presence of a base as a reaction catalyst to obtain the diol compound of Formula 12. The reaction may be carried out at a temperature of 2 to 30° C., 5 to 20° C., or 5 to 15° C. for 2 to 10 hours, 2 to 8 hours, or 2 to 5 hours. Furthermore, the amount of 2-mercaptoethanol may be 0.5 mole to 3 moles, particularly 0.7 mole to 2 moles, more particularly 0.9 mole to 1.1 moles, per 1 mole of the halogenated styrene oxide. The base may be used in a catalytic amount. Specifically, the amount of the base may be 0.001 mole to 0.1 mole per 1 mole of the halogenated styrene oxide in case the base is monovalent, and it may be half of the amount of the monovalent base in case the base is bivalent. Here, the base as the reaction catalyst may be triethylamine, tributylamine, or the like and may be used in the form of an aqueous solution or an alcoholic solution. When the base is used in the form of an aqueous solution or an alcoholic solution, the concentration of the base solution may be properly selected.

In step (2), the diol compound of Formula 12 may be reacted with a metal sulfide in a solvent to prepare a tetraol compound represented by Formula 13. The reaction may be carried out at a temperature of 10 to 50° C., particularly 20 to 40° C., for 1 to 10 hours, 1 to 8 hours, or 1 to 5 hours. The metal sulfide may be, for example, sodium sulfide ($Na_2S$). The metal sulfide may be used in the form of an aqueous solution or solid and is preferably used in the form of a hydrate, but is not limited thereto. When the metal sulfide is used in the form of an aqueous solution, it is preferable to adjust its concentration to 10 to 80%, particularly 30 to 60%. The metal sulfide may be used in an amount of 0.4 to 0.6 mole, particularly 0.45 to 0.57 mole, more particularly 0.48 to 0.55 mole, per 1 mole of the diol compound of Formula 12.

In step (3), the tetraol compound of Formula 13 thus obtained may be reacted with thiourea to prepare an isothiouronium salt, which is then hydrolyzed to prepare the compound of Formula 10. First, the compound of Formula 13 is mixed with thiourea with reflux in an acidic condition to prepare an isothiouronium salt. Thiourea may be used in an amount of 3 moles or more, particularly 3 moles to 6 moles, more particularly 4.6 moles to 5 moles, per 1 mole of the tetraol compound. For the acidic condition, a hydrochloric acid solution, a hydrogen chloride gas, or the like may be used in an amount of 3 moles or more, particularly 3 to 12 moles, per 1 mole of the tetraol compound of Formula 13 above. By using hydrogen chloride, a sufficient reaction rate can be secured, and coloring of the product can be prevented. The reflux may be carried out at 90 to 120° C., preferably at 100 to 110° C., for 1 to 10 hours.

Subsequently, the isothiouronium salt thus prepared is hydrolyzed in an organic solvent in a basic condition to prepare the aromatic polythiol compound of Formula 10.

Specifically, while the reaction solution containing the isothiouronium salt is maintained at 20 to 60° C., particularly 25 to 55° C., more particularly 25 to 50° C., a basic aqueous solution is added to the reaction solution for 80 minutes or less, 70 minutes or less, 20 to 60 minutes, or 20 to 30 minutes. The time for adding the basic aqueous solution is preferably as short as possible, but is set within the above-mentioned time range in view of the cooling facility, equipment, and the like. The basic aqueous solution is not limited as long as it is a basic substance that can be dissolved in water and generate a hydroxyl group (—OH), such as ammonia, sodium hydroxide, potassium hydroxide, calcium hydroxide, magnesium hydroxide, and aluminum hydroxide. The concentration of the basic aqueous solution may be 10 to 70%, particularly 15 to 50%. Here, an organic solvent may be added before the basic aqueous solution is added. The organic solvent can suppress formation of by-products. The organic solvent may be added in an amount of 0.1 to 3.0 times, particularly 0.2 to 2.0 times, the amount of the isothiouronium salt reaction solution. Examples of the organic solvent include toluene, xylene, chlorobenzene, dichlorobenzene, and the like and may be particularly toluene. The basic substance may be used in an amount of 1 mole or more, particularly 1 mole to 3 moles, more particularly 1.1 moles to 2 moles, per 1 mole of the hydrogen chloride. Here, the basic substance may be added at a rate of 1.25 mol %/min or more, particularly 1.25 mol %/min to 3.75% mol/min, more particularly 1.38 mol %/min to 2.5 mol %/min. The hydrolysis temperature may be 10 to 130° C., particularly 30 to 80° C. The hydrolysis time may be 0.1 to 24 hours, particularly 0.5 to 12 hours, more particularly from 1 to 8 hours.

The aromatic polythiol compound thus prepared may be further purified.

For example, it may be subjected to several times of alkali washing and several times of water washing. Impurities or the like remaining in the polythiol can be removed through the washing process, which improves the color of the polythiol and the color of the optical material prepared therefrom.

Thereafter, if desired, the aromatic polythiol compound may be subjected to drying, filtration, and the like.

An embodiment provides a polymerizable composition comprising the aromatic polythiol compound (C) and an isocyanate-based compound.

The polymerizable composition may comprise the aromatic polythiol compound in an amount of 100% by weight. If necessary, the polymerizable composition may further comprise a polythiol compound different from the aromatic polythiol compound in addition to the aromatic polythiol compound (C) as described above, which may be an aliphatic polythiol compound. The aliphatic polythiol compound may be methanedithiol, 1,2-ethanedithiol, 1,2,3-propanetriethiol, pentaerythritol tetrakis(2-mercaptoacetate), pentaerythritol tetrakis(3-mercaptopropionate), bis(mercaptoethyl) sulfide, 2,5-dimercaptomethyl-1,4-dithiane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl) sulfide, 2,5-dimercaptomethyl-1,4-dithiane, 2,5-dimercapto-1,4-dithiane, 2,5-dimercaptomethyl-2,5-dimethyl-1,4-dithiane, 1,1,3,3-tetrakis(mercaptomethylthio)propane, 1,1,2,2-tetrakis(mercaptomethylthio)ethane, 4,6-bis(mercaptomethylthio)-1,3-dithiane, or the like.

When the polymerizable composition further comprises a polythiol compound different from the aromatic polythiol compound, the aromatic polythiol compound may be in an amount of 5 to 70 parts by weight based on 100 parts by weight of the total thiol compounds.

The isocyanate-based compound may be a conventional one commonly used for the synthesis of polythiourethane. Specific examples of the isocyanate-based compound are as exemplified above.

Furthermore, the polymerizable composition may further comprise an additive as described above, depending on the purpose thereof.

An embodiment provides a process for producing an optical material by polymerizing and molding the polymerizable composition as described above. Further, an optical material produced by the above preparation process is provided. The optical material may be produced by polymerizing and molding the polymerizable composition in accordance with the process as described above.

The optical material is produced by polymerizing (and curing) the aromatic polythiol compound and the isocyanate compound. The reaction molar ratio of SH groups to NCO groups in the polymerization reaction may be 0.5 to 3.0, particularly 0.6 to 2.0, more particularly 0.8 to 1.3. Further, the above-mentioned reaction catalyst, which is conventionally used in the production of polythiourethane, may be employed in order to control the reaction rate.

The optical material may have a refractive index of 1.60 to 1.75, 1.60 to 1.70, 1.63 to 1.75, or 1.63 to 1.70. The optical material may have a specific gravity of 1.10 to 1.30, 1.15 to 1.30, or 1.20 to 1.30. The optical material may have a heat distortion temperature (Tg) of 100 to 120° C., 110 to 120° C., or 113 to 120° C.

The optical material may particularly be an optical lens, specifically a plastic optical lens.

If required, the optical lens may be subjected to physical or chemical treatment such as surface polishing, antistatic treatment, hard coat treatment, anti-reflection coat treatment, dyeing treatment, dimming treatment for the purpose of imparting thereto anti-reflection, hardness, abrasion resistance, chemical resistance, anti-fogging, or fashionity.

Aromatic Polythiol Compound D

An embodiment provides an aromatic polythiol compound (D) represented by any one of Formulae 14 to 16 below:

[Formula 14]

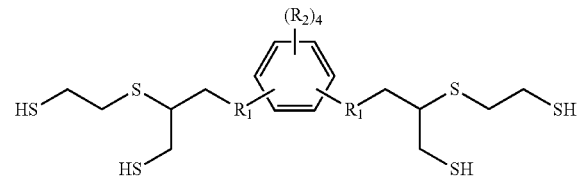

[Formula 15]

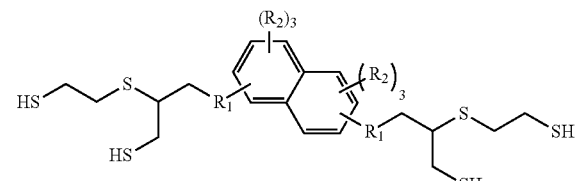

[Formula 16]

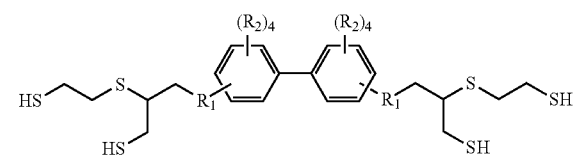

In these formulae, $R_1$ is each independently a sulfur atom or an oxygen atom, and $R_2$ is each independently a hydrogen atom, a halogen atom, $C_{1-10}$ alkyl, or $C_{6-10}$ aryl.

Specifically, $R_2$ each independently may be a hydrogen atom, a halogen atom, $C_{1-6}$ alkyl, or phenyl.

In the above aromatic polythiol compounds, the $R_1$ substituent may be combined to any carbon atom constituting the aromatic ring. For example, the compound of Formula 14 may be an ortho, meta, or para type isomer. Specifically, the aromatic polythiol compound may have substituents in a symmetrical structure.

The aromatic polythiol compound represented by any one of Formulae 14 to 16 may be prepared by preparing an aromatic polyol compound from an aromatic compound having one or two phenyl groups and then reacting the aromatic polyol compound with thiourea and hydrolyzing the reaction product.

Specifically, the aromatic polythiol compound of Formula 14 may be prepared by the steps of (1) reacting a compound of Formula 17 with epichlorohydrin to prepare a compound having a structure of chlorohydrin as represented by Formula 18; (2) reacting the compound of Formula 18 with 2-mercaptoethanol to prepare an aromatic polyol compound having a structure of polyhydric alcohol as represented by Formula 19; and (3) reacting the aromatic polyol compound of Formula 19 with thiourea to prepare an isothiouronium salt and hydrolyzing the isothiouronium salt (see Reaction Scheme 4).

[Reaction Scheme 4]

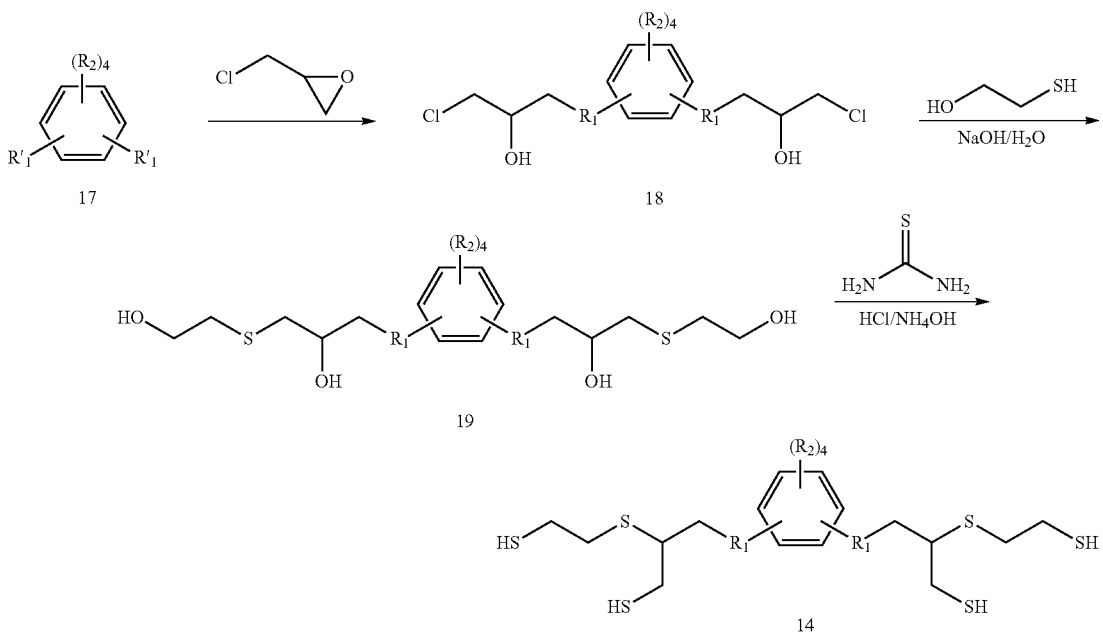

In this scheme, $R_1'$ is each independently hydroxy or thiol, and $R_1$ and $R_2$ each are as defined in Formula 14 above.

The aromatic polythiol compound of Formula 15 may be prepared by the steps of (1') reacting a compound represented by Formula 20 with epichlorohydrin to produce a compound having a structure of chlorohydrin as represented by Formula 21; (2') reacting the compound of Formula 21 with 2-mercaptoethanol to prepare an aromatic polyol compound having a structure of polyhydric alcohol as represented by Formula 22; and (3') reacting the aromatic polyol compound of Formula 22 with thiourea to prepare an isothiouronium salt and hydrolyzing the isothiouronium salt (see Reaction Scheme 5).

[Reaction Scheme 5]

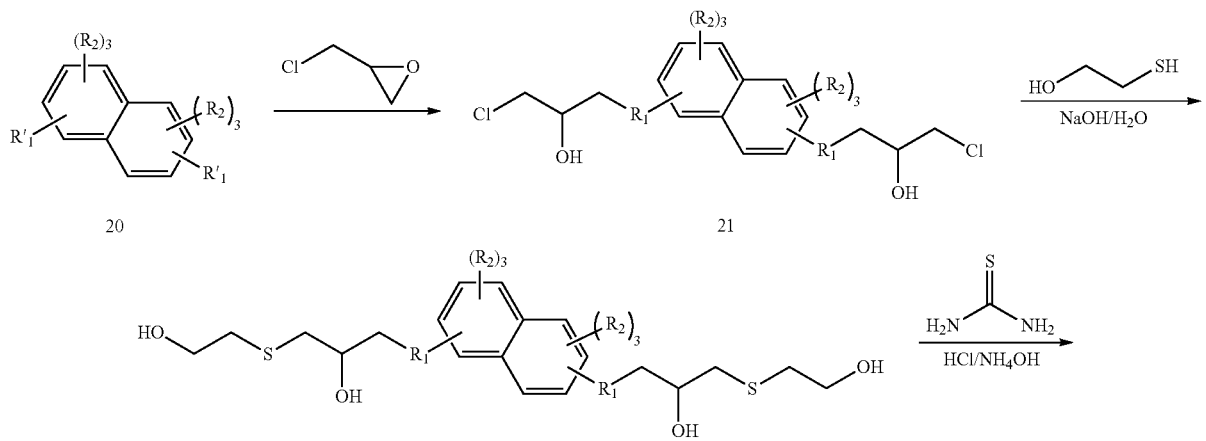

-continued

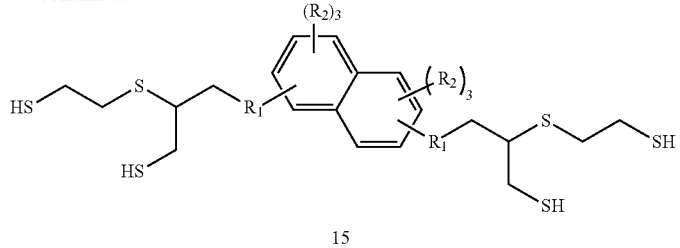

15

In this scheme, $R_1$, $R_1'$, and $R_2$ each are as defined in Formulae 15 and 17 above.

The aromatic polythiol compound of Formula 16 may be prepared by the steps of (1″) reacting a compound represented by Formula 23 with epichlorohydrin to prepare a compound having a structure of chlorohydrin as represented by Formula 24; (2″) reacting the compound of Formula 24 with 2-mercaptoethanol to prepare an aromatic polyol compound having a structure of polyhydric alcohol as represented by Formula 25; and (3″) reacting the aromatic polyol compound of Formula 25 with thiourea to prepare an isothiouronium salt and hydrolyzing the isothiouronium salt (see Reaction Scheme 6).

C. Epichlorohydrin may be reacted in an amount of 0.8 to 1.2 equivalents per 1 equivalent of the compound of Formula 17, 20, or 23.

Steps (2), (2′), and (2″) above may be carried out by reacting the compound of Formula 18, 21, or 24 with 2-mercaptoethanol in water in the presence of a base to prepare the aromatic polyol compound of Formula 19, 22, or 25. As the base, sodium hydroxide; potassium hydroxide; a tertiary amine such as trimethylamine and triethylamine; a secondary amine such as dimethylamine and diethylamine; a primary amine such as methylamine and ethylamine; ammonia; or the like may be used. The reaction may be carried out at 40 to 100° C., particularly at 50 to 60° C.

[Reaction Scheme 6]

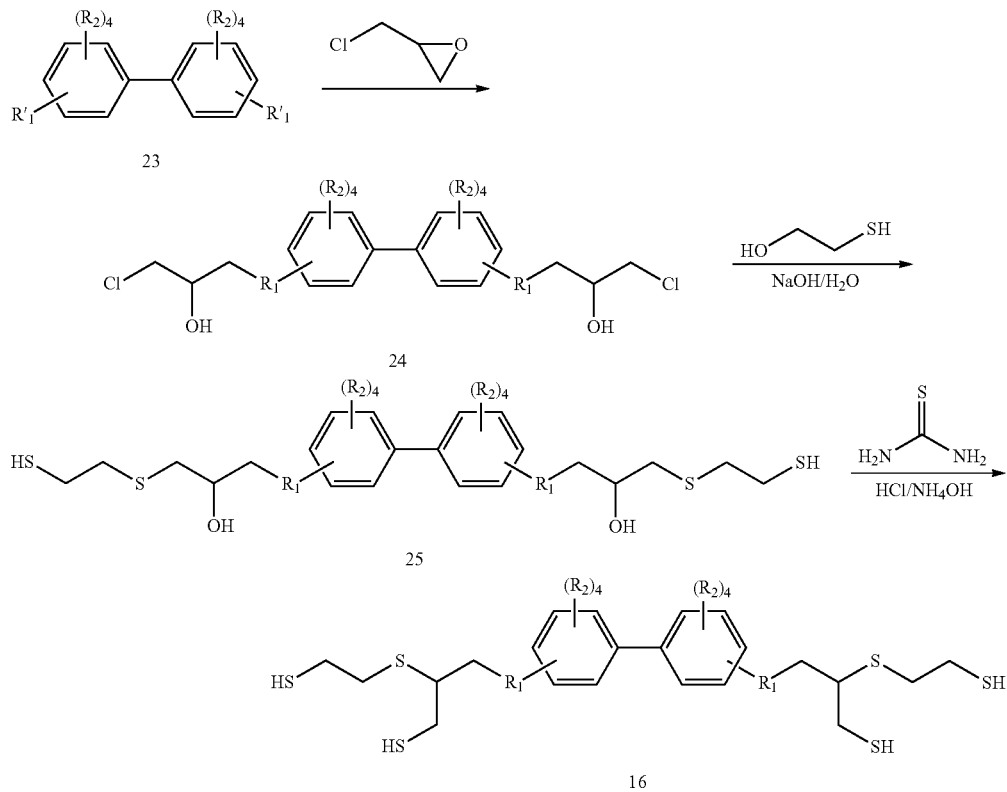

In this scheme, $R_1$, $R_1'$, and $R_2$ each are as defined in Formulae 16 and 17 above.

Steps (1), (1′), and (1″) above may be carried out in water in the presence of a catalyst such as triethylamine, sodium hydroxide, potassium hydroxide, chromium octoate, or triphenylphosphine at 40 to 100° C., particularly at 50 to 60°

2-Mercaptoethanol may be reacted in an amount of 0.8 to 1.2 equivalents per 1 equivalent of the compound of Formula 18, 21, or 24.

In steps (3), (3′), and (3″) above, the aromatic polyol compound of Formula 19, 22, or 25 is mixed with thiourea with reflux in an acidic condition to prepare an isothiouronium salt. Thiourea may be reacted in an amount of 1 to 3 equivalents, particularly 1 to 2 equivalents, per 1 equivalent of hydroxyl groups in the aromatic polyol compound. For the acidic condition, an aqueous hydrochloric acid solution, hydrogen chloride gas, or the like may be used. The temperature during the reflux may be 60 to 130° C., particularly 90 to 120° C. The reflux time may be 2 to 24 hours, particularly 2 to 12 hours.

Subsequently, the isothiouronium salt is hydrolyzed in an organic solvent to prepare the aromatic polythiol compound of any one of Formulae 14 to 16. Examples of the organic solvent include toluene, xylene, chlorobenzene, and dichlorobenzene. To suppress formation of by-products, toluene is preferred. The hydrolysis temperature may be 10 to 130° C., particularly 30 to 80° C. The hydrolysis time may be 0.1 to 24 hours, particularly 0.5 to 12 hours.

The aromatic polythiol compound thus prepared may be further purified.

For example, it may be subjected to several times of acid washing and several times of water washing. Impurities or the like remaining in the polythiol can be removed through the washing process, which improves the color of the polythiol and the color of the optical material prepared therefrom.

Thereafter, if desired, the aromatic polythiol compound may be subjected to drying, filtration, and the like.

The aromatic polythiol compound prepared above may have a thiol value (SHV or SH value) of 100 to 400 g/eq. Further, the aromatic polythiol compound contains a phenyl group and a large number of sulfur atoms in its structure. Thus, it may be subsequently reacted with an isocyanate to produce a polythiourethane-based optical material that has excellent optical properties such as high refractive index and low specific gravity, as well as excellent mechanical properties such as low cure shrinkage.

An embodiment provides a polymerizable composition comprising the aromatic polythiol compound (D) and an isocyanate-based compound. Here, the polymerizable composition may further comprise a polythiol compound different from the aromatic polythiol compound in addition to the aromatic polythiol compound (D) as described above.

The isocyanate-based compound may be a conventional one commonly used for the synthesis of polythiourethane. Specific examples of the isocyanate-based compound are as exemplified above.

Furthermore, the polymerizable composition may further comprise such additives as an internal mold release agent, a heat stabilizer, a reaction catalyst, an ultraviolet absorber, and a blueing agent, as described above, depending on the purpose thereof.

An embodiment provides a process for producing an optical material by polymerizing and molding the polymerizable composition as described above. Further, an optical material produced by the above preparation process is provided. The optical material may be produced by polymerizing and molding the polymerizable composition in accordance with the process as described above.

The optical material is produced by polymerizing (and curing) the aromatic polythiol compound and the isocyanate compound. The reaction molar ratio of SH groups to NCO groups in the polymerization reaction may be 0.5 to 3.0, particularly 0.5 to 1.5, more particularly 0.8 to 1.5. Further, the above-mentioned reaction catalyst, which is conventionally used in the production of polythiourethane, may be employed in order to control the reaction rate.

The optical material may have a refractive index of 1.60 to 1.75, 1.60 to 1.68, 1.63 to 1.70, or 1.63 to 1.68. The optical material may have a specific gravity of 1.10 to 1.30, 1.10 to 1.25, 1.20 to 1.30, or 1.20 to 1.25. The optical material may have a heat distortion temperature (Tg) of 100 to 120° C., 100 to 110° C., 105 to 120° C., or 105 to 110° C.

The optical material may preferably be an optical lens, specifically a plastic optical lens.

As described above, the aromatic polythiol compounds according to the embodiments, for example, any one or more of the aromatic polythiol compounds A to D contain a phenyl group and a large number of sulfur atoms in their polythiol structures. Thus, a polythiourethane prepared from the aromatic polythiol compounds has excellent optical properties such as high refractive index and low specific gravity, as well as excellent mechanical properties such as low cure shrinkage, which is preferably used in the manufacture of various plastic optical lenses such as eyeglass lenses and camera lenses.

MODE FOR THE INVENTION

Hereinafter, the present invention is explained in detail by Examples. The following Examples are intended to further illustrate the present invention without limiting its scope.

EXAMPLE

Preparation of Bi- or Higher-Functional Aliphatic Polythiol Compounds

Preparation Example 1

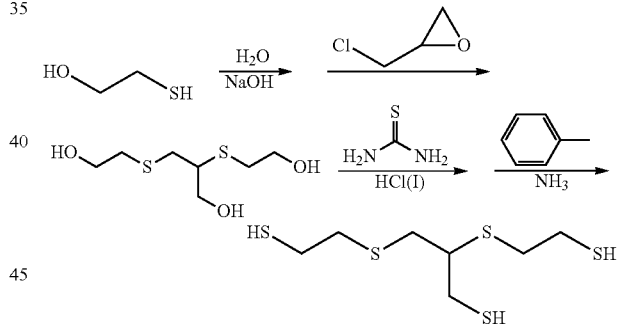

124.6 parts by weight of 2-mercaptoethanol and 18.3 parts by weight of distilled water were charged into a reactor, and 101.5 parts by weight of an aqueous sodium hydroxide solution (32%) were added dropwise at about 23° C. for 40 minutes. 73.6 parts by weight of epichlorohydrin were added dropwise at about 32° C. for 4.5 hours, followed by stirring the mixture for 40 minutes to obtain 2,3-bis(2-hydroxyethylthio)-1-propanol.

331.5 parts by weight of hydrochloric acid (35.5%) were added to the above compound, and 183.8 parts by weight of thiourea (99.90%) were added thereto, followed by stirring the mixture at 110° C. for 3 hours with reflux for carrying out the reaction for an isothiouronium salt. After the reaction mixture was cooled to 45° C., 320.5 parts by weight of toluene were added thereto. After the reaction mixture was cooled to 31° C., 243.1 parts by weight of an aqueous ammonia solution (25%) were added dropwise at about 36° C. for 44 minutes, followed by stirring the reaction mixture at about 58° C. for 3 hours to obtain a reaction solution.

162.8 parts by weight of hydrochloric acid (35.5%) were added to the reaction solution thus prepared, which was then subjected to acid washing at about 39° C. for 1 hour. Thereafter, 174.1 parts by weight of distilled water were added thereto, and washing was performed at about 40° C. for 30 minutes, which washing was repeated twice. 162.1 parts by weight of an aqueous ammonia solution (0.1%) were added thereto, which was then subjected to washing for 30 minutes. Then, 174.2 parts by weight of distilled water were added thereto, and washing was performed at about 40° C. for 30 minutes, which washing was repeated twice. Toluene and a small amount of water were removed from the reaction solution under heating and reduced pressures, and then the reaction solution was filtered under reduced pressures through a membrane filter of 1.2 μm PTFE type to obtain 205.0 parts by weight of 4-mercaptomethyl-1,8-dimercapto-3,6-dithiaoctane. The elemental analysis of the obtained compound showed C (32.2), H (6.2), and S (61.6) as similar to the theoretical values. The $^1$H-NMR (CDCl$_3$) analysis showed δ ppm=1.74-1.91 (3H, m, SH) and 2.70-3.00 (13H, m, CH). The FT-IR analysis showed the stretching peak of SH at 2541 cm$^{-1}$.

Preparation Example 2 prepare 1-chloro-3-(2-hydroxyethylthio)-2-propanol. 150 parts by weight of am aqueous sodium sulfide solution (17.3%) were added dropwise to the above compound at about 22° C. for 5.5 hours, followed by stirring the mixture for 120 minutes to obtain a reaction solution. 279 parts by weight of hydrochloric acid (35.5%) were added to the reaction solution, and then 125.8 parts by weight of thiourea were added thereto, followed by stirring the reaction solution at about 110° C. for 3 hours with reflux for carrying out the reaction for an isothiouronium salt. After the reaction mixture was cooled to 45° C., 214 parts of toluene were added thereto. After the reaction mixture was cooled to 26° C., 206.2 parts by weight of an aqueous ammonia solution (25%) were added dropwise at about 38° C. for 30 minutes, followed by stirring the mixture at about 57° C. for 1 hours to obtain a reaction solution.

59.4 parts by weight of hydrochloric acid (35.5%) were added to the reaction solution thus prepared, which was then subjected to acid washing at about 37° C. for 30 minutes. This acid washing was repeated twice. Thereafter, 118.7 parts by weight of degassed water (dissolved oxygen concentration: 2 ppm) were added thereto, and washing was performed at about 40° C. for 30 minutes, which washing was repeated 5 times. Toluene and a small amount of water were removed from the reaction solution under heating and reduced pressures, and then the mixture was filtered under reduced pressures through a membrane filter of 1.2 μm PTFE type to obtain 5,9-dimercaptomethyl-1,13-di-

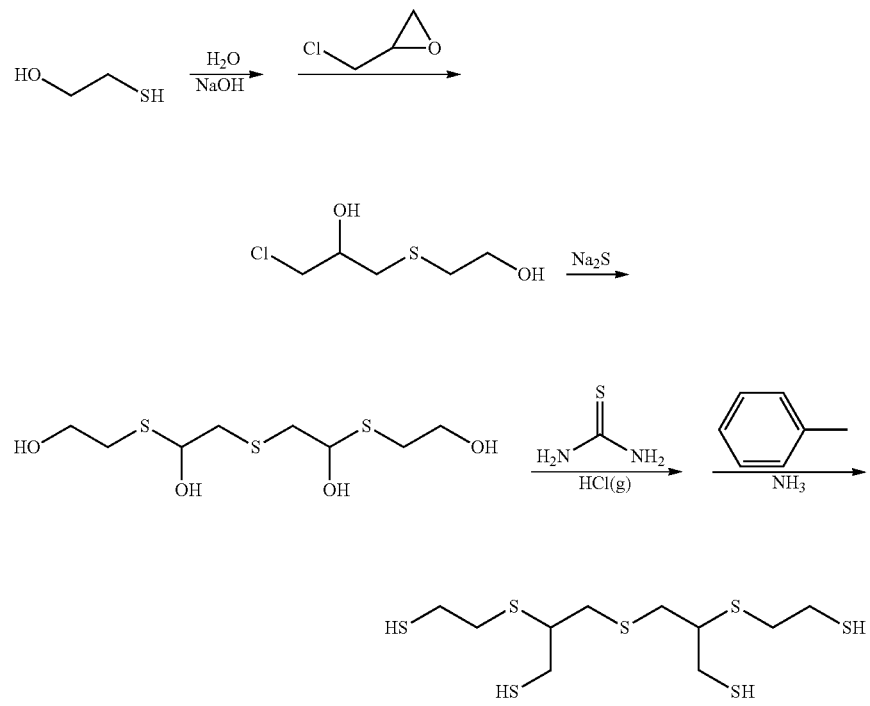

51.2 parts by weight of 2-mercaptoethanol, 26.5 parts by weight of distilled water, and 0.16 part by weight of an aqueous sodium hydroxide solution (49% by weight) were charged into a reactor, and then 61.99 parts by weight of epichlorohydrin were added dropwise at about 10° C. for 6.5 hours, followed by stirring the mixture for 60 minutes to mercapto-3,7,11-trithiatridecane. The elemental analysis of the obtained compound showed C (32.9), H (6.1), and S (61.0) as similar to the theoretical values. The $^{13}$C-NMR (CDCl$_3$) analysis showed δ ppm=35.1-35.9 (—SCH$_2$—), 24.9 (—CH$_2$SH), and 48.7 (—CH—). The FT-IR analysis showed the stretching peak of SH at 2541 cm$^{-1}$.

Preparation of Aromatic Polythiol Compound A

Example 1

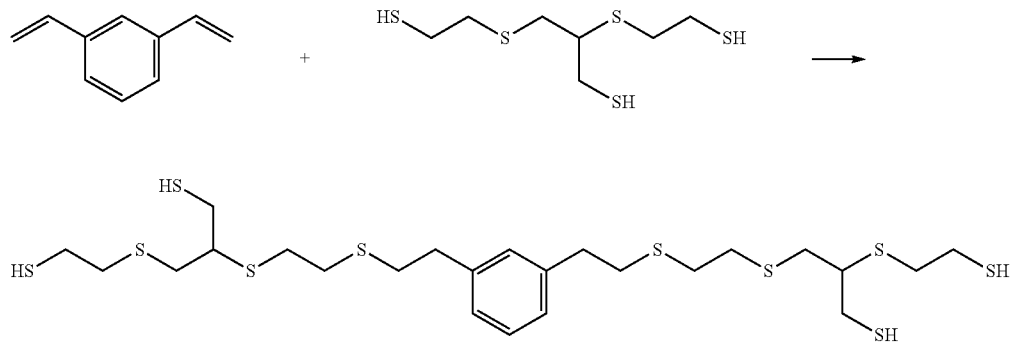

130 g (1 mole) of divinylbenzene, 650 g (2.5 moles) of the polythiol compound of Preparation Example 1, and 3.5 g of azobisisobutyronitrile (AIBN) were charged into a reactor and reacted at 80° C. for 5 hours. When the characteristic peak of a double bond at 1680 cm$^{-1}$ in FT-IR completely disappeared, the reaction was terminated to obtain a tetrafunctional aromatic polythiol compound. The main peak of this compound in the gel permeation chromatography (GPC) analysis indicated a number average molecular weight of 1,100.

Details of the GPC analysis are shown in Table 1 below.

TABLE 1

| Model | Waters APC system |
|---|---|
| Column | 2 Acquity APC XT Columns 45A (4.6 * 150 mm) |

TABLE 1-continued

| Column temperature | 45° C. |
|---|---|
| Mobile phase | THF |
| Flow rate | 0.5 ml/min |
| Total rum time | 10 min |
| Injection volume | 10 μl |
| Detector | RID, 40° C. |

Example 2

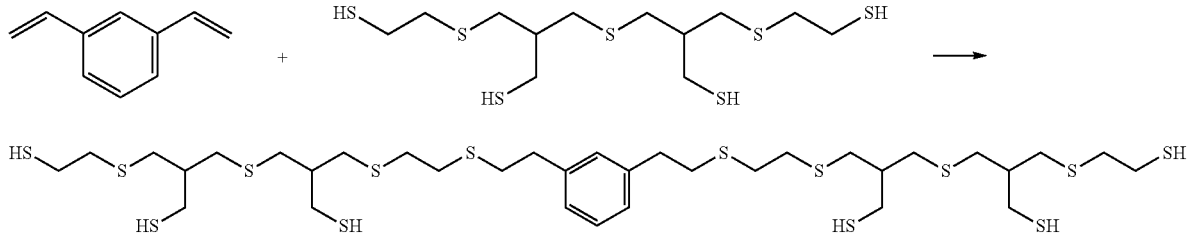

The reaction was carried out in the same manner as in Example 1, except that 985 g (2.5 moles) of the polythiol compound of Preparation Example 2 were used, to thereby obtain a hexafunctional aromatic polythiol compound. The main peak of this compound in the GPC analysis indicated a number average molecular weight of 1,400.

Example 3

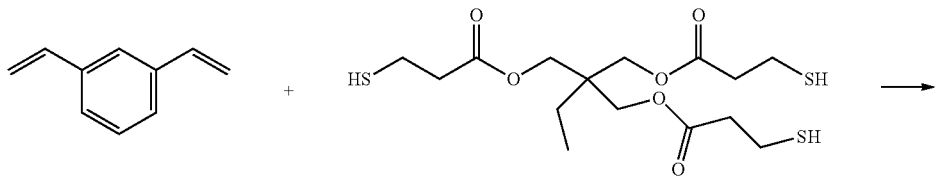

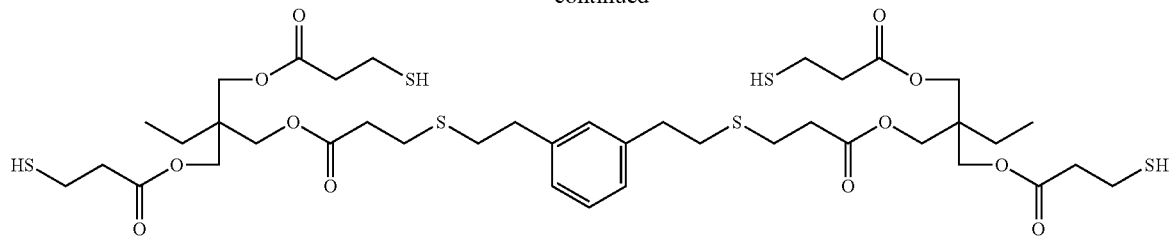

The reaction was carried out in the same manner as in Example 1, except that 995 g (2.5 moles) of trimethylolpropane tri(3-mercaptopropionate) (TMPMP) from Bruno Bock were used, to thereby obtain a tetrafunctional aromatic polythiol compound. The main peak of this compound in the GPC analysis indicated a number average molecular weight of 1,600.

Example 4

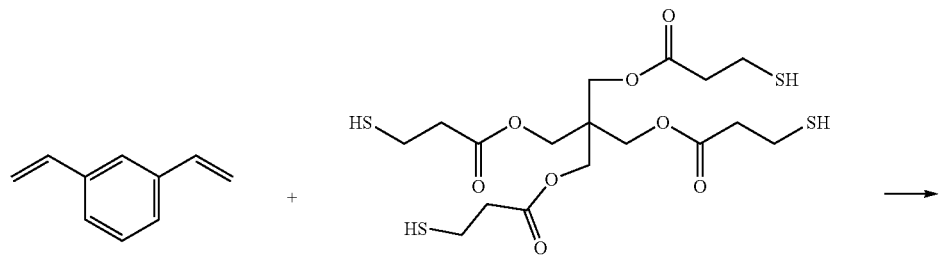

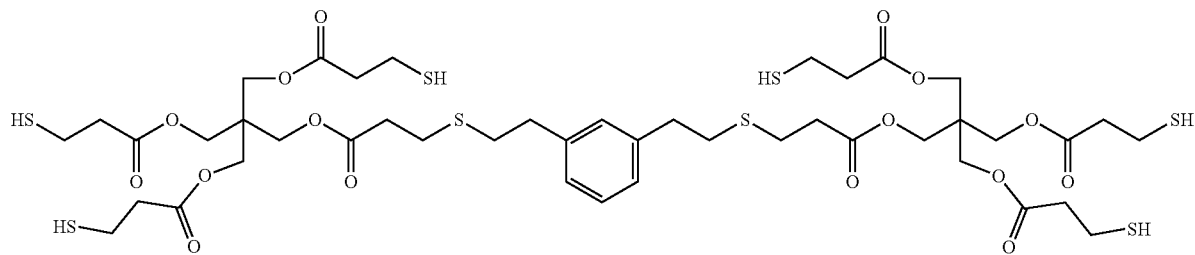

The reaction was carried out in the same manner as in Example 1, except that 1,223 g (2.5 moles) of pentaerythritol tetrakis(3-mercaptopropionate) (PETMP) from Bruno Bock were used, to thereby obtain a hexafunctional aromatic polythiol compound. The main peak of this compound in the GPC analysis indicated a number average molecular weight of 1,800.

Preparation of a Polymerizable Composition from Aromatic Polythiol Compound A

Example 5

56.5 parts by weight of the tetrafunctional aromatic polythiol compound prepared in Example 1 above were uniformly mixed with 43.5 parts by weight of 1,3-bis(isocyanatomethyl)cyclohexane (Takenate® 600). 1 part by weight of 1-hydroxy-4-(p-toluidine)anthraquinone as a bluing agent, 0.01 part by weight of dibutyltin dichloride as a polymerization catalyst, 0.1 part by weight of Zelec® UN as an internal mold release agent, and 0.05 parts by weight of CYASORB® UV-5411 as an ultraviolet absorber were added thereto and uniformly mixed to prepare a polymerizable composition.

Examples 6 to 11 and Comparative Examples 1 to 4

Polymerizable compositions were prepared in the same manner as in Example 5, except that the components and their contents (parts by weight) were changed as shown in Table 2 below.

Test Example 1: Property Measurement

The properties of the polymerizable compositions prepared in Examples 5 to 11 and in Comparative Examples 1 to 4 were measured in accordance with the methods as described below. The measurement results are shown in Table 2 below.

(1) Refractive Index

The polymerizable compositions prepared in Examples 5 to 11 and in Comparative Examples 1 to 4 each were degassed at 600 Pa for 1 hour and then filtered through a Teflon filter of 3 μm. The filtered polymerizable composition was injected into a glass mold assembled by tapes. The mold was heated from 25° C. to 120° C. at a rate of 5° C./min, and polymerization was carried out at 120° C. for 18 hours. The cured resin in the glass mold was further cured at 130° C. for 4 hours, and then the molded article was released from the glass mold. The molded article was a circular lens (optical material) having a center thickness of 1.2 mm (deviation: −5.00) and a diameter of 72 mm. The lens was impregnated in a ST11TN-8H hard coating solution (Finecoat Co.) and then thermally cured for coating it.

The refractive index of the lens was measured at 20° C. using an Abbe refractometer DR-M4 (Atago Co.).

(2) Specific Gravity

The weight to volume ratio of the optical lens described in Section (1) above was measured by a water displacement method, from which its specific gravity was calculated.

(3) Heat Resistance (Heat Distortion)

The glass transition temperature (Tg; or heat distortion temperature) of the optical lens described in Section (1) above was measured with TMA Q400 (TA Co.) under the penetration method (load of 50 g, pin line of 0.5 mm 4, temperature elevation rate of 10° C./min).

(4) Light Resistance (Difference in Yellowness Indices Before and after Exposure to Light; ΔYI)

Molded articles were made from the polymerizable compositions prepared in Examples 5 to 11 and in Comparative Examples 1 to 4 in the same manner as in Section (1) above, except that the circular lens (optical material) thus produced had a thickness of 9 mm and a diameter of 75 mm. No coating was applied on to the lens. The chromaticity coordinates x and y of the optical material were measured using a spectrophotometer CM-5 manufactured by Minolta Co., from which its yellow index (YI) was calculated with Equation (1) below. Then, the optical material was exposed to a QUV/Spray model (5w) of Q-Pannel Lab Products for 200 hours, followed by measurement of the yellow index in the same manner as described above. The difference in YI values (i.e., difference in YI values before and after light exposure) was calculated and indicated as light resistance (ΔYI).

$$YI = (234x + 106y + 106)/y \quad \text{[Equation 1]}$$

TABLE 2

| | | Ex. 5 | Ex. 6 | Ex. 7 | Ex. 8 | Ex. 9 | Ex. 10 | Ex. 11 | CEx. 1 | CEx. 2 | CEx. 3 | CEx. 4 |
|---|---|---|---|---|---|---|---|---|---|---|---|---|
| Takenate ® 600 | | 43.5 | 45.2 | 34.5 | 29.5 | 33.5 | | | 47.2 | 38.7 | | |
| Takenate ® 500 | | | | | | | 42.8 | 33.8 | | | | |
| TDI | | | | | | | | | | | 44.5 | 36.2 |
| Prep. Ex. 1 | | | | | | | | | 52.8 | | 55.5 | |
| Prep. Ex. 2 | | | | | | 26.5 | | | | 61.3 | | 63.8 |
| Ex. 1 | | 56.5 | | | | | 57.2 | | | | | |
| Ex. 2 | | | 54.8 | | | | | | | | | |
| Ex. 3 | | | | 65.5 | | | | 66.2 | | | | |
| Ex. 4 | | | | | 70.5 | 40.0 | | | | | 53.2 | |
| DYE | | 1 | 1 | 1 | 1 | 1 | 1 | 1 | 1 | 1 | 1 | 1 |
| DBTDC | | 0.01 | 0.01 | 0.01 | 0.01 | 0.01 | 0.01 | 0.01 | 0.01 | 0.01 | 0.01 | 0.01 |
| Zelec ® UN | | 0.1 | 0.1 | 0.1 | 0.1 | 0.1 | 0.1 | 0.1 | 0.1 | 0.1 | 0.1 | 0.1 |
| CYASORB ® UV-5411 | | 0.05 | 0.05 | 0.05 | 0.05 | 0.05 | 0.05 | 0.05 | 0.05 | 0.05 | 0.05 | 0.05 |
| Measured values | Refractive index (nd20) | 1.64 | 1.64 | 1.59 | 1.59 | 1.62 | 1.69 | 1.63 | 1.59 | 1.59 | 1.68 | 1.68 |
| | Specific gravity | 1.21 | 1.22 | 1.21 | 1.22 | 1.22 | 1.21 | 1.21 | 1.31 | 1.32 | 1.29 | 1.28 |
| | Heat distortion (Tg) | 115 | 116 | 112 | 110 | 114 | 124 | 115 | 96 | 93 | 102 | 97 |
| | Heat resistance (ΔYI) | 1.1 | 1.2 | 1.3 | 1.2 | 1.1 | 2.4 | 2.5 | 1.1 | 1.2 | 8.4 | 7.9 |

Takenate ® 600: 1,3-bis(isocyanatomethyl)cyclohexane
Takenate ® 500: xylene diisocyanate
TDI: toluene diisocyanate
DYE: 1-hydroxy-4-(p-toluidine)anthraquinone
DBTDC: dibutyltin dichloride
Zelec ® UN: phosphoric acid ester releasing agent, Stepan Co.
CYASORB ® UV-5411: 2-(2'-hydroxy-5'-t-octylphenyl) benzotriazole, Cytec As shown in Table 2 above, the optical lenses of Examples 5 to 11 have low specific gravity, high heat distortion temperature, and excellent light resistance represented by a small chromaticity difference, as compared with the optical lenses of Comparative Examples 1 to 4. The refractive indices of the optical lenses of the Examples and of the Comparative Examples were similar to each other. Thus, the optical lenses produced in the Examples would be advantageously used as optical materials because they are lightweight, withstand at high temperatures, and form a clear image.

Preparation of Aromatic Polythiol Compound B

Example 12

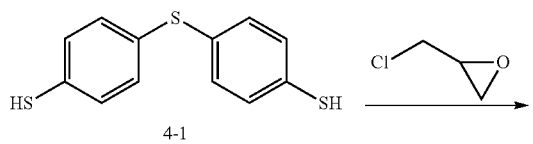

4-1

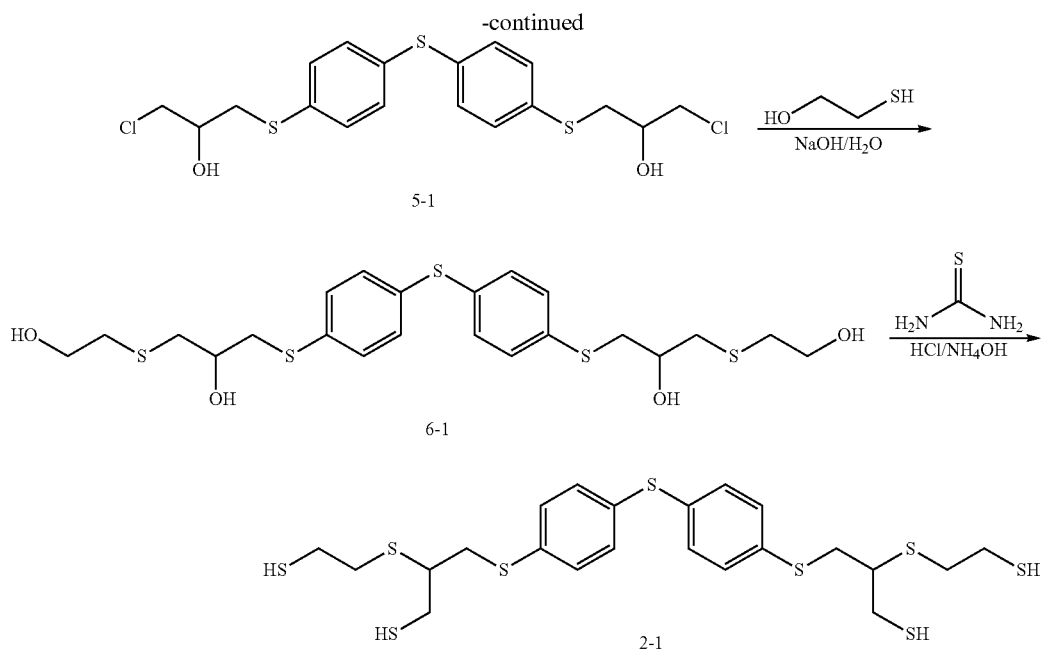

250 g (1 mole) of 4,4-thiobisbenzenethiol, 435 g of water, and 0.5 g of triethylamine were charged into a three-necked, five-liter reactor equipped with a mechanical stirrer and a cooling tube, and the temperature was maintained at 50° C. Then, 185 g (2 moles) of epichlorohydrin were added dropwise to the reactor for 1 hour, and the mixture was aged at 60° C. for 5 hours to obtain a reaction solution. When epichlorohydrin was not detected from the reaction solution as a result of thin layer chromatograph (TLC), the reaction was terminated to obtain the compound of Formula 5-1 having a chlorohydrin structure.

A mixture of 500 g of water, 156 g (2 moles) of 2-mercaptoethanol, and 100 g (2 moles) of 80% sodium hydroxide was slowly added dropwise to the compound of Formula 5-1 at 50° C. for 2 hours, followed by aging of the mixture at 60° C. for 3 hours to obtain a reaction solution. When 2-mercaptoethanol was not detected from the reaction solution as a result of TLC, the reaction was terminated to obtain the aromatic polyol compound of Formula 6-1.

576 g (6 moles) of a 38% concentrated hydrochloric acid solution were added to the aromatic polyol compound of Formula 6-1 obtained above, and 335 g (4.4 moles) of thiourea were added thereto, followed by reaction for a thiouronium salt at 110° C. for 3 hours with reflux. Then, the reaction solution was cooled to 40° C., and 650 g of toluene were added to the reaction solution, followed by cooling it to 25° C. Thereafter, 637 g (4.5 moles) of a 25% aqueous ammonia solution were added dropwise to the reaction solution at 50° C. for 30 minutes, and the reaction solution was further subjected to hydrolysis at 60° C. for 1 hour.

After the toluene portion of the reaction solution was separated, 127 g of a 38% concentrated hydrochloric acid solution were added to the toluene portion and admixed. After 30 minutes, the water portion was removed using a separating funnel. This acid washing was repeated twice. Next, 255 g of distilled water were added to the reaction solution that had been subjected to the acid washing and admixed. After 30 minutes, the water portion was removed using a separating funnel. This water washing was repeated five times. Then, toluene and a small amount of water were completely removed through a heating and depressurizing process, and the reaction solution was then filtered through a Teflon filter of 1 μm to obtain the tetrafunctional aromatic polythiol compound of Formula 2-1.

H-NMR: ppm 1.7 (2H, —SH), 2.7-3.3 (9H, —SCH$_2$—), 7.0 (4H, —SCH$_2$=CH$_2$—), 7.1 (—CH$_2$=CH$_2$—).

Example 13

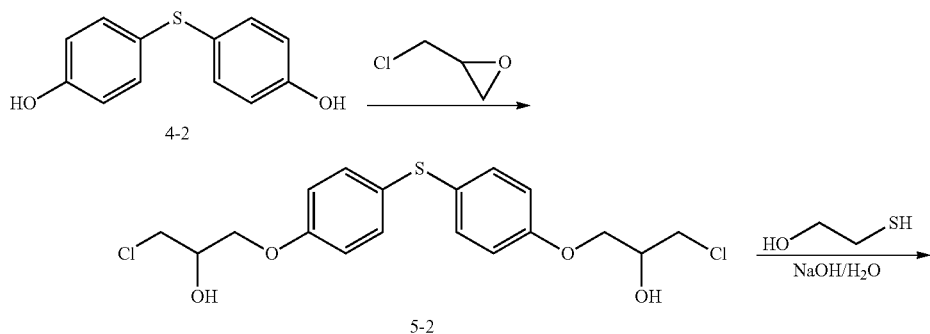

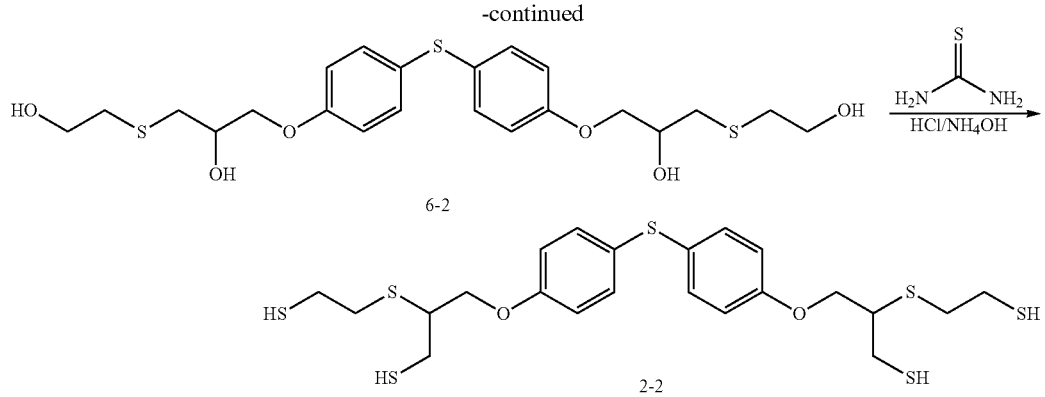

6-2

2-2

The reaction was carried out in the same manner as in Example 12, except that 218 g (1 mole) of 4,4-thiophenol were used instead of 250 g (1 mole) of 4,4-thiobisbenzenethiol, to thereby obtain the tetrafunctional aromatic polythiol compound of Formula 2-2.

H-NMR: ppm 1.7 (2H, —SH), 2.7-3.4 (7H, —SCH$_2$—), 4.1-4.4 (2H, —CH$_2$O—), 6.6 (4H, —OCH$_2$=CH$_2$—), 7.1 (4H, —CH$_2$=CH$_2$—).

Example 14

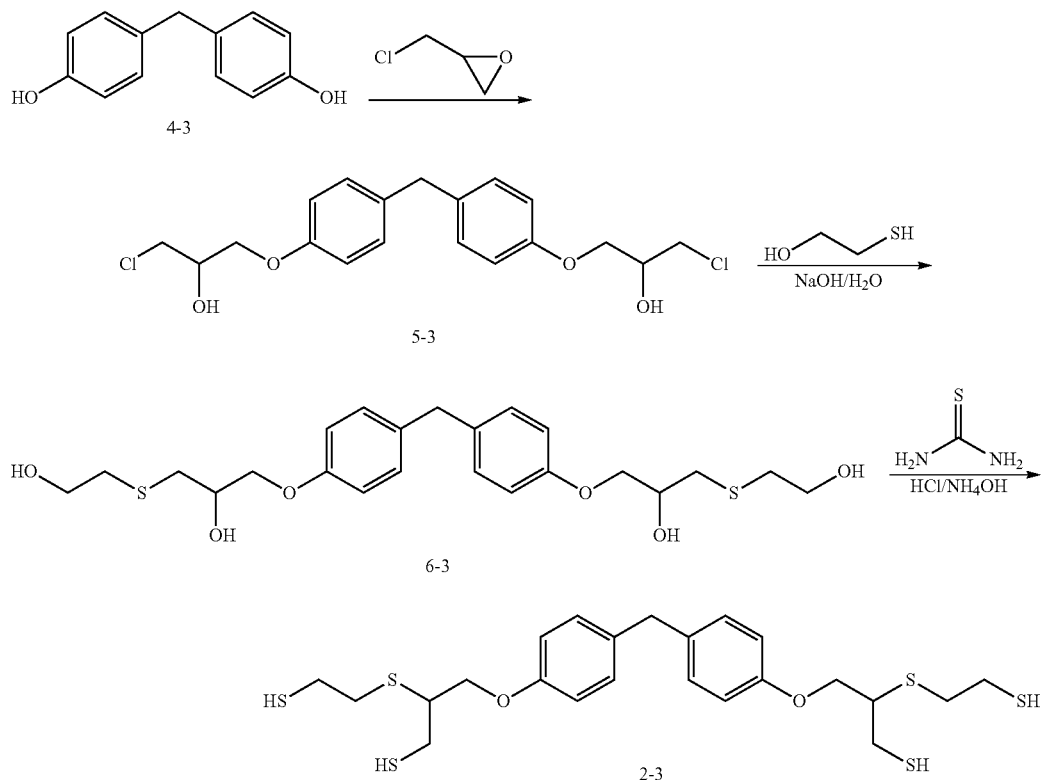

4-3

5-3

6-3

2-3

The reaction was carried out in the same manner as in Example 12, except that 200 g (1 mole) of bisphenol F were used instead of 250 g (1 mole) of 4,4-thiobisbenzenethiol, to thereby obtain the tetrafunctional aromatic polythiol compound of Formula 2-3.

H-NMR: ppm 1.7 (2H, —SH), 2.7-3.4 (7H, —SCH$_2$—), 3.9 (2H, —CH$_2$—), 4.1-4.4 (2H, —CH$_2$O—), 6.6 (4H, —OCH$_2$=CH$_2$—), 7.0 (4H, —CH$_2$=CH$_2$—).

Preparation of a Polymerizable Composition from Aromatic Polythiol Compound B

Example 15

61.2 parts by weight of the aromatic polythiol compound prepared in Example 12 above were uniformly mixed with 38.8 parts by weight of 1,3-bis(isocyanatomethyl)cyclohexane (Takenate® 600). 0.01 part by weight of dibutyltin dichloride as a polymerization catalyst, 0.1 part by weight of Zelec® UN as an internal mold release agent, and 0.05 part by weight of CYASORB® UV-5411 as an ultraviolet absorber were added thereto and uniformly mixed to prepare a polymerizable composition.

Examples 16 to 19 and Comparative Examples 5 to 8

Polymerizable compositions were prepared in the same manner as in Example 15, except that the components and their contents (parts by weight) were changed as shown in Table 3 below.

Test Example 2: Property Measurement

The properties of the polymerizable compositions prepared in Examples 15 to 19 and in Comparative Examples 5 to 8 were measured with the same methods as described above. The measurement results are shown in Table 3 below.

TABLE 3

|  |  | Ex. 15 | Ex. 16 | Ex. 17 | Ex. 18 | Ex. 19 | CEx. 5 | CEx. 6 | CEx. 7 | CEx. 8 |
|---|---|---|---|---|---|---|---|---|---|---|
| Takenate ® 600 | | 38.8 | 40.1 | 40.9 | | 39.8 | 49.8 | 52.0 | | |
| Takenate ® 500 | | | | | 40.2 | | | | | |
| TDI | | | | | | | | | 46.8 | 50.1 |
| Ex. 12 | | 61.2 | | | | 31.4 | | | | |
| Ex. 13 | | | 59.9 | | | | | | | |
| Ex. 14 | | | | 59.1 | 59.8 | 28.8 | | | | |
| Aliphatic polythiol A | | | | | | | 51.2 | | 53.2 | |
| Aliphatic polythiol B | | | | | | | | 48.0 | | 49.9 |
| DBTDC | | 0.01 | 0.01 | 0.01 | 0.01 | 0.01 | 0.01 | 0.01 | 0.01 | 0.01 |
| Zelec ® UN | | 0.1 | 0.1 | 0.1 | 0.1 | 0.1 | 0.1 | 0.1 | 0.1 | 0.1 |
| CYASORB ® UV-5411 | | 0.05 | 0.05 | 0.05 | 0.05 | 0.05 | 0.05 | 0.05 | 0.05 | 0.05 |
| Measured values | Refractive index (nd20) | 1.69 | 1.65 | 1.59 | 1.67 | 1.64 | 1.59 | 1.59 | 1.67 | 1.67 |
| | Specific gravity | 1.21 | 1.22 | 1.22 | 1.21 | 1.21 | 1.31 | 1.32 | 1.33 | 1.33 |
| | Heat distortion (Tg) | 114 | 115 | 114 | 119 | 115 | 99 | 101 | 105 | 102 |
| | Heat resistance (ΔYI) | 3.1 | 1.9 | 1.7 | 3.4 | 2.5 | 1.4 | 1.5 | 7.4 | 6.9 |

Aliphatic polythiol A: 5,9-dimercaptomethyl-1,13-dimercapto-3,7,11-trithiatridecane
Aliphatic polythiol B: 2,3-bis(2-mercaptoethylthio)-propane-1-thiol As shown in Table 3 above, the optical lenses of Examples 15 to 19 have low specific gravity, high heat distortion temperature, and excellent light resistance represented by a small chromaticity difference, as compared with the optical lenses of Comparative Examples 5 to 8. The refractive indices of the optical lenses of the Examples and of the Comparative Examples were similar to each other. Thus, the optical lenses produced in the Examples would be advantageously used as optical materials because they are lightweight, withstand at high temperatures, and form a clear image.

Preparation of Aromatic Polythiol Compound C

Example 20

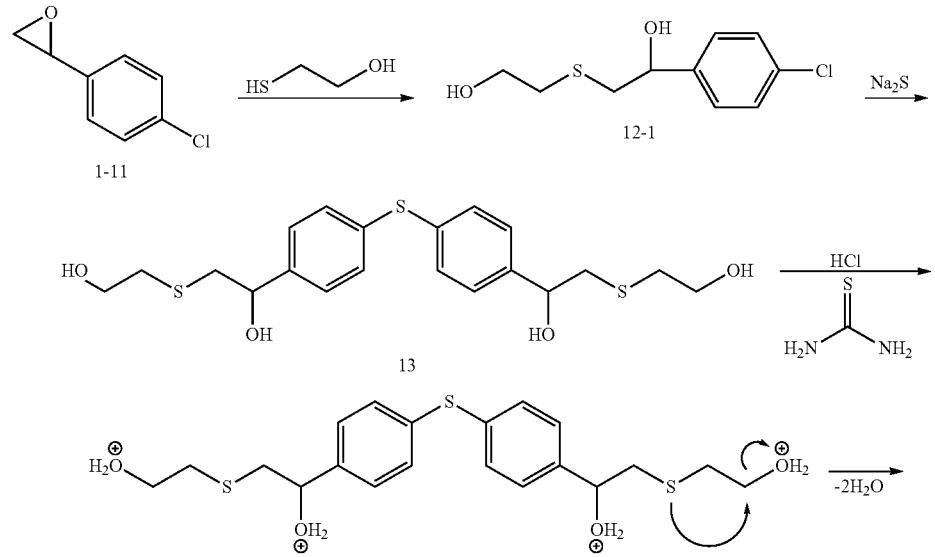

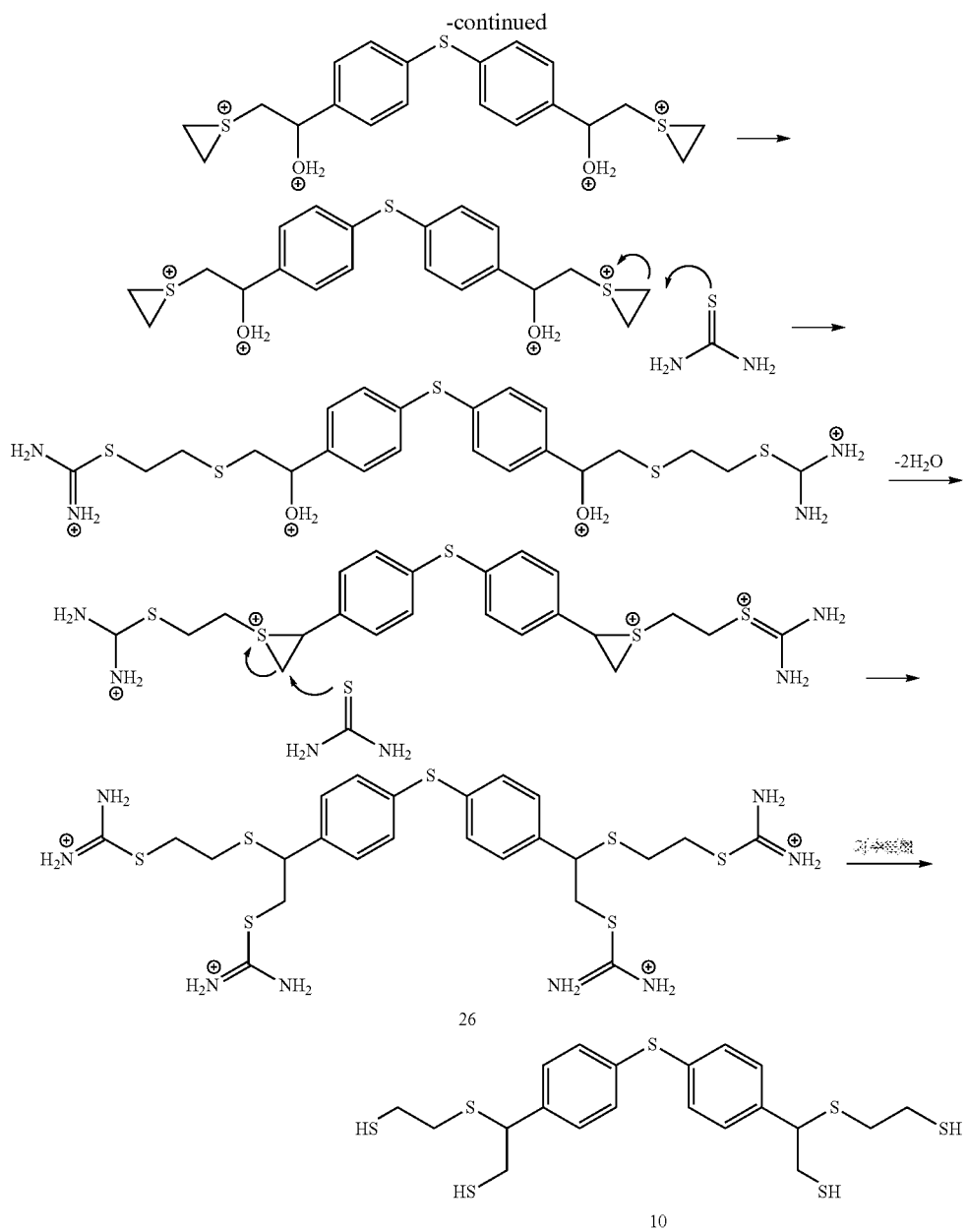

-continued 154.6 g (1 mole) of 4-chlorostyrene oxide, 78.13 g (1 mole) of 2-mercaptoethanol, and 0.1 g of triethylamine were charged into a three-necked, five-liter reactor equipped with a mechanical stirrer and a cooling tube, and the temperature was maintained at 8° C. for 4 hours to obtain a reaction solution comprising the compound of Formula 12-1. When 2-mercaptoethanol was not detected from the reaction solution as a result of thin layer chromatograph (TLC), the reaction was terminated.

A mixture of 124.9 g (0.52 mole) of sodium sulfide nonahydrate and 124.9 g of water was slowly added dropwise to the reaction solution at 30° C. for 3 hours, followed by aging of the reaction solution at 40° C. for 1 hour to obtain a reaction solution comprising the compound of Formula 13. When the compound of Formula 12-1 was not detected from the reaction solution as a result of TLC, the reaction was terminated.

576 g (6 moles) of a 38% concentrated hydrochloric acid solution were added to the reaction solution, and then 335 g (4.4 moles) of thiourea were added thereto, followed by reaction for a thiouronium salt at 110° C. for 3 hours with reflux to obtain a reaction solution comprising the compound of Formula 5.

After the reaction solution was cooled to 40° C., 650 g of toluene were added thereto, followed by cooling it to 25° C. Thereafter, 637 g (4.5 moles) of a 25% aqueous ammonia solution were added dropwise to the reaction solution at 50° C. for 30 minutes, and the reaction solution was further subjected to hydrolysis at 60° C. for 1 hour.

After the toluene portion of the reaction solution was separated, 127 g of a 38% concentrated hydrochloric acid solution were added to the toluene portion and admixed. After 30 minutes, the water portion was removed using a separating funnel (i.e., acid washing process). This acid washing was repeated twice. Next, 255 g of distilled water were added to the reaction solution that had been subject to the acid washing and admixed. After 30 minutes, the water portion was removed using a separating funnel. This water washing was repeated five times. Then, toluene and a small amount of water were completely removed through a heating and depressurizing process, and the reaction solution was then filtered through a Teflon filter of 1 μm to obtain the tetrafunctional aromatic polythiol compound of Formula 10. The results of FT-IR and $C^{13}$-NMR analyses on the aromatic polythiol compound thus obtained are as follows.

TABLE 4

|   | Theoretical value | Measured value |
|---|---|---|
| C | 50.5% | 51.0% |
| H | 6.6% | 6.8% |
| S | 42.9% | 42.2% |

FT-IR: IR $\lambda_{max}$ (KBr) cm$^{-1}$ = 2600 (SH)

TABLE 5

| $C_{13}$-NMR | ppm |
|---|---|
| (structural formula shown) | a = 26.8 |
|  | b = 33.5 |
|  | c = 48.7 |
|  | d = 34.7 |
|  | e = 137.5 |
|  | f = 129.4 |
|  | g = 131.1 |
|  | h = 134.1 |

Preparation of a Polymerizable Composition from Aromatic Polythiol Compound C

Example 21

72.8 parts by weight of the aromatic polythiol compound prepared in Example 20 above were uniformly mixed with 27.2 parts by weight of 1,3-bis(isocyanatomethyl)cyclohexane (Takenate® 600). 0.01 part by weight of dibutyltin dichloride as a polymerization catalyst, 0.1 part by weight of Zelec® UN as an internal mold release agent, and 0.05 part by weight of CYASORB® UV-5411 as an ultraviolet absorber were added thereto and uniformly mixed to prepare a polymerizable composition.

Examples 22 and 23 and Comparative Examples 9 and 10

Polymerizable compositions were prepared in the same manner as in Example 21, except that the components and their contents (parts by weight) were changed as shown in Table 6 below.

Test Example 3: Property Measurement

The properties of the polymerizable compositions prepared in Examples 21 to 23 and in Comparative Examples 9 and 10 were measured with the same methods as described above. The measurement results are shown in Table 6 below.

TABLE 6

|  |  | Ex. 21 | Ex. 22 | Ex. 23 | CEx. 9 | CEx. 10 |
|---|---|---|---|---|---|---|
| Takenate ® 600 | | 27.2 | | | 49.8 | 52.0 |
| Takenate ® 500 | | | 26.6 | | | |
| TDI | | | | 30.0 | | |
| Ex. 20 | | 72.8 | 73.4 | 70.0 | | |
| Aliphatic polythiol A | | | | | 51.2 | |
| Aliphatic polythiol B | | | | | | 48.0 |
| DBTDC | | 0.01 | 0.01 | 0.01 | 0.01 | 0.01 |
| Zelec ® UN | | 0.1 | 0.1 | 0.1 | 0.1 | 0.1 |
| CYASORB ® UV-5411 | | 0.05 | 0.05 | 0.05 | 0.05 | 0.05 |
| Measured values | Refractive index (nd20) | 1.65 | 1.69 | 1.64 | 1.59 | 1.59 |
|  | Specific gravity | 1.21 | 1.25 | 1.22 | 1.31 | 1.32 |
|  | Heat distortion (Tg) | 114 | 118 | 109 | 102 | 97 |
|  | Heat resistance (ΔYI) | 1.6 | 1.9 | 1.8 | 1.6 | 1.5 |

As shown in Table 6 above, the optical lenses of Examples 21 to 23 have low specific gravity, high refractive index, high heat distortion temperature, and excellent light resistance represented by a small chromaticity difference, as compared with the optical lenses of Comparative Examples 9 and 10. Thus, the optical lenses produced in the Examples would be advantageously used as optical materials because they are lightweight, withstand at high temperatures, and form a clear image.

Preparation of Aromatic Polythiol Compound D

Example 24

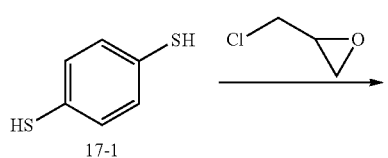

17-1

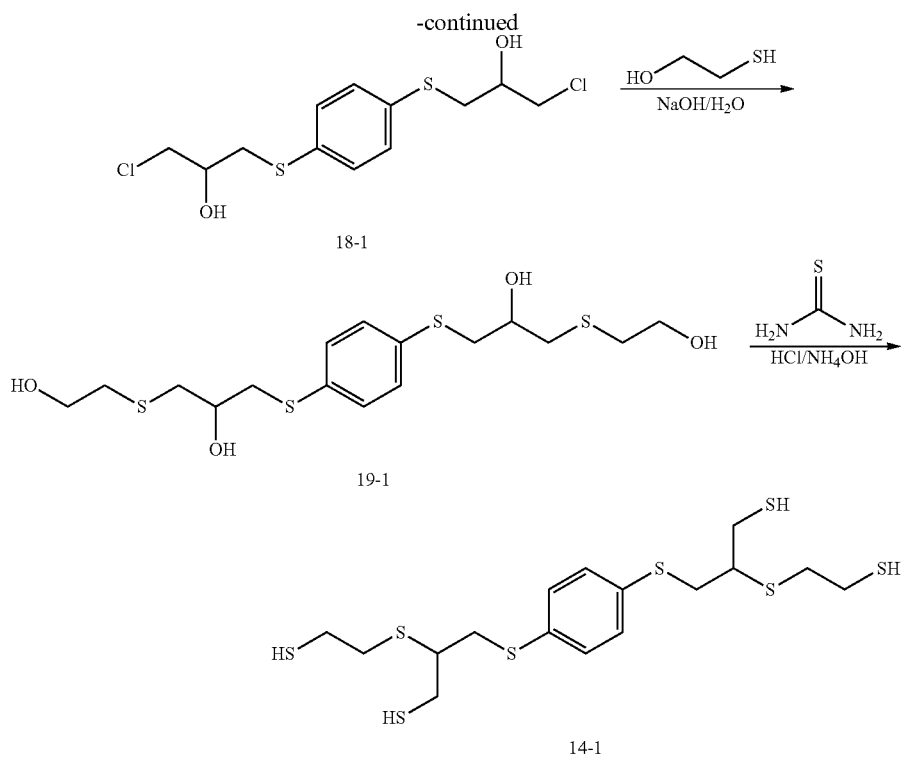

142 g (1 mole) of 1,4-benzenedithiol, 435 g of water, and 0.5 g of triethylamine were charged into a three-necked, five-liter reactor equipped with a mechanical stirrer and a cooling tube, and the temperature was maintained at 50° C. Then, 185 g (2 moles) of epichlorohydrin were added dropwise to the reactor for 1 hour, and the mixture was aged at 60° C. for 5 hours to obtain a reaction solution. When epichlorohydrin was not detected from the reaction solution as a result of thin layer chromatograph (TLC), the reaction was terminated to obtain the compound of Formula 18-1 having a chlorohydrin structure.

A mixture of 500 g of water, 156 g (2 moles) of 2-mercaptoethanol, and 100 g (2 moles) of 80% sodium hydroxide was slowly added dropwise to the compound of Formula 18-1 at 50° C. for 2 hours, followed by aging of the mixture at 60° C. for 3 hours to thereby obtain a reaction solution. When 2-mercaptoethanol was not detected from the reaction solution as a result of TLC, the reaction was terminated to thereby obtain the aromatic polyol compound of Formula 19-1.

576 g (6 moles) of a 38% concentrated hydrochloric acid solution were added to the aromatic polyol compound of Formula 19-1, and then 335 g (4.4 moles) of thiourea were added thereto, followed by reaction for a thiouronium salt at 110° C. for 3 hours with reflux. Then, the reaction solution was cooled to 40° C., and 650 g of toluene were added to the reaction solution, followed by cooling it to 25° C. Thereafter, 637 g (4.5 moles) of a 25% aqueous ammonia solution were added dropwise to the reaction solution at 50° C. for 30 minutes, and the reaction solution was further subjected to hydrolysis at 60° C. for 1 hour.

After the toluene portion of the reaction solution was separated, 127 g of a 38% concentrated hydrochloric acid solution were added to the toluene portion and admixed. After 30 minutes, the water portion was removed using a separating funnel. This acid washing was repeated twice. Next, 255 g of distilled water were added to the reaction solution that had been subjected to the acid washing and admixed. After 30 minutes, the water portion was removed using a separating funnel. This water washing was repeated five times. Then, toluene and a small amount of water were completely removed through a heating and depressurizing process, and the reaction solution was then filtered through a Teflon filter of 1 μm to obtain the tetrafunctional aromatic polythiol compound of Formula 14-1.

H-NMR (ppm): 1.6 (2H, —SH), 2.7-3.4 (9H, —CH$_2$S—), 7.2 (4H, —CH$_2$=)

FT-IR: 2540 cm$^{-1}$ (—SH)

TABLE 7

| <Elemental analysis> | | |
|---|---|---|
| | Theoretical value | Measured value |
| C | 40.5% | 40.1% |
| H | 5.5% | 5.6% |
| S | 54.0% | 54.4% |

Example 25

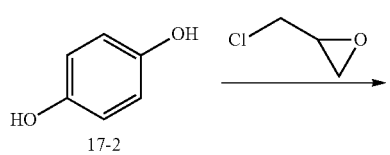

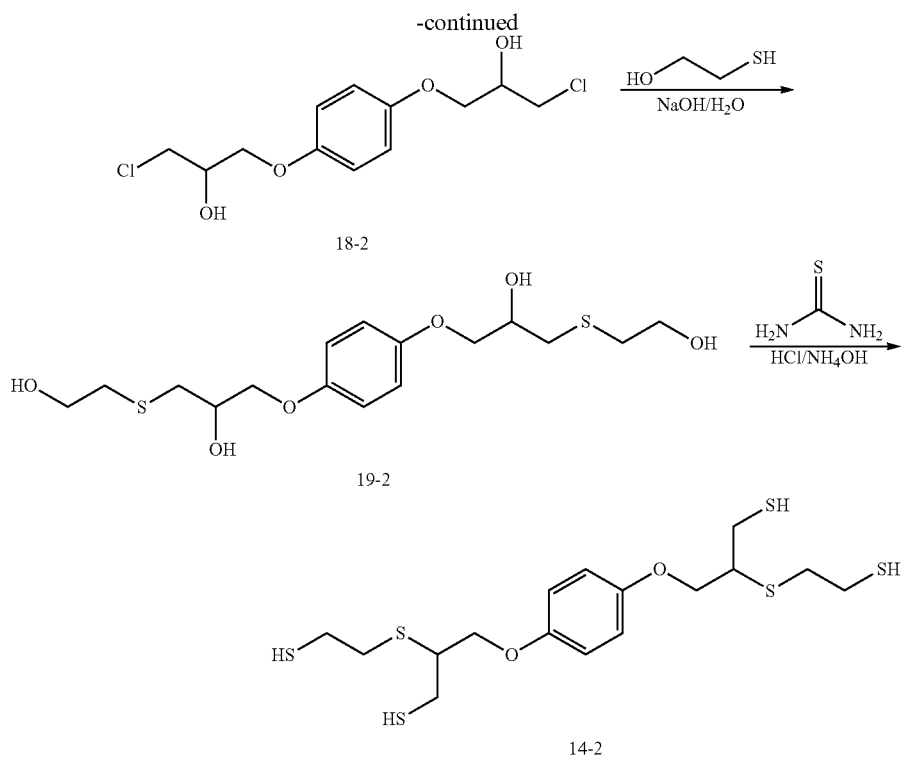

The reaction was carried out in the same manner as in Example 24, except that 110 g (1 mole) of hydroquinone were used instead of 142 g (1 mole) of 1,4-benzenedithiol, to thereby obtain the tetrafunctional aromatic polythiol compound of Formula 14-2.

H-NMR (ppm): 1.6 (2H, —SH), 2.7-3.4 (7H, —CH$_2$S—), 4.1-4.4 (2H, —CH$_2$O—), 6.7 (4H, —CH$_2$=)

FT-IR: 2540 cm$^{-1}$ (—SH)

TABLE 8

<Elemental analysis>

| | Theoretical value | Measured value |
|---|---|---|
| C | 43.4% | 43.6% |
| H | 5.9% | 5.7% |
| O | 7.2% | 7.1% |
| S | 43.5% | 43.6% |

Preparation of a Polymerizable Composition from Aromatic Polythiol Compound D

Example 26

56.5 parts by weight of the aromatic polythiol compound prepared in Example 24 above were uniformly mixed with 43.5 parts by weight of 1,3-bis(isocyanatomethyl)cyclohexane (Takenate® 600). 0.01 part by weight of dibutyltin dichloride as a polymerization catalyst, 0.1 part by weight of Zelec® UN as an internal mold release agent, and 0.05 part by weight of CYASORB® UV-5411 as an ultraviolet absorber were added thereto and uniformly mixed to thereby prepare a polymerizable composition.

Examples 27 and Comparative Examples 11 to 13

Polymerizable compositions were prepared in the same manner as in Example 26, except that the components and their contents (parts by weight) were changed as shown in Table 9 below.

Test Example 4: Property Measurement

The properties of the polymerizable compositions prepared in Examples 26 and 27 and in Comparative Examples 11 to 14 were measured with the same methods as described above. The measurement results are shown in Table 9 below.

TABLE 6

| | Ex. 26 | Ex. 27 | CEx. 11 | CEx. 12 | CEx. 13 | CEx. 14 |
|---|---|---|---|---|---|---|
| Takenate ® 600 | 43.5 | 45.2 | 49.8 | 52.0 | | |
| TDI | | | | | 46.8 | 50.1 |
| Ex. 24 | 56.5 | | | | | |
| Ex. 25 | | 54.8 | | | | |
| Aliphatic polythiol A | | | 51.2 | | 53.2 | |
| Aliphatic polythiol B | | | | 48.0 | | 49.9 |
| DBTDC | 0.01 | 0.01 | 0.01 | 0.01 | 0.01 | 0.01 |
| Zelec ® UN | 0.1 | 0.1 | 0.1 | 0.1 | 0.1 | 0.1 |

TABLE 6-continued

|  |  | Ex. 26 | Ex. 27 | CEx. 11 | CEx. 12 | CEx. 13 | CEx. 14 |
|---|---|---|---|---|---|---|---|
| CYASORB ® UV-5411 | | 0.05 | 0.05 | 0.05 | 0.05 | 0.05 | 0.05 |
| Measured values | Refractive index (nd20) | 1.68 | 1.64 | 1.59 | 1.59 | 1.67 | 1.67 |
| | Specific gravity | 1.21 | 1.22 | 1.31 | 1.32 | 1.33 | 1.33 |
| | Heat distortion (Tg) | 109 | 110 | 99 | 101 | 105 | 102 |
| | Heat resistance (ΔYI) | 2.8 | 1.7 | 1.4 | 1.5 | 7.4 | 6.9 |

As shown in Table 9 above, the optical lenses of Examples 26 and 27 have low specific gravity, high heat distortion temperature, and excellent light resistance represented by a small chromaticity difference, as compared with the optical lenses of Comparative Examples 11 to 14. The refractive indices of the optical lenses of the Examples and of the Comparative Examples were similar to each other. Thus, the optical lenses produced in the Examples would be advantageously used as optical materials because they are lightweight, withstand at high temperatures, and form a clear image.

The invention claimed is:

1. An aromatic polythiol compound prepared by reacting a divinylbenzene compound represented by Formula 1 below and a bi- or higher-functional aliphatic polythiol,
    wherein the bi- or higher-functional aliphatic polythiol is at least one selected from the group consisting of ethoxylated trimethylolpropane tri(3-mercaptopropionate), tris[2-(3-mercaptopropionyloxy)ethyl]isocyanurate, dipentaerythritol hexa(3-mercaptopropionate), and 5,9-dimercaptomethyl-1,13-dimercapto-3,7,11-trithiatridecane, and
    wherein the molar ratio of the divinylbenzene compound to the bi- or higher-functional aliphatic polythiol is 1:2 to 1:10:

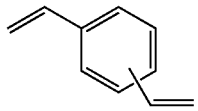

[Formula 1]

2. An aromatic polythiol compound prepared by reacting a divinylbenzene compound represented by Formula 1 below and a bi- or higher-functional aliphatic polythiol,
    wherein the aromatic polythiol compound has a number average molecular weight of 500 to 3,000, and
    wherein the bi- or higher-functional aliphatic polythiol is at least one selected from the group consisting of ethoxylated trimethylolpropane tri(3-mercaptopropionate), tris[2-(3-mercaptopropionyloxy)ethyl]isocyanurate, dipentaerythritol hexa(3-mercaptopropionate), and 5,9-dimercaptomethyl-1,13-dimercapto-3,7,11-trithiatridecane:

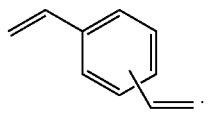

[Formula 1]

* * * * *